US012797205B2

(12) United States Patent
Reah et al.

(10) Patent No.: US 12,797,205 B2
(45) Date of Patent: Nov. 17, 2026

(54) INTERVERTEBRAL DEVICES

(71) Applicant: AXIS SPINE TECHNOLOGIES LTD, Reading (GB)

(72) Inventors: Christopher Reah, Reading (GB); Jonathan Arcos, Reading (GB); Nicholas Sandham, Reading (GB); David Powell, Reading (GB); John Sutcliffe, Reading (GB); Patrick McKenna, Reading (GB); Frank Heuer, Reading (GB)

(73) Assignee: AXIS SPINE TECHNOLOGIES LTD, Reading (GB)

( * ) Notice: Subject to any disclaimer, the term of this patent is extended or adjusted under 35 U.S.C. 154(b) by 9 days.

(21) Appl. No.: 18/928,707

(22) Filed: Oct. 28, 2024

(65) Prior Publication Data

US 2025/0186221 A1 Jun. 12, 2025

Related U.S. Application Data

(63) Continuation-in-part of application No. 17/430,711, filed as application No. PCT/GB2020/050328 on Feb.

(Continued)

(30) Foreign Application Priority Data

Nov. 19, 2018 (GB) ...................................... 1818849
Feb. 13, 2019 (GB) ...................................... 1902002

(51) Int. Cl.
*A61F 2/44* (2006.01)
*A61F 2/46* (2006.01)
*A61F 2/30* (2006.01)

(52) U.S. Cl.
CPC .... *A61F 2/447* (2013.01); *A61F 2002/30537* (2013.01)

(58) Field of Classification Search
CPC .......... A61F 2/447; A61F 2/446; A61F 2/442; A61F 2/44; A61F 2002/30537
(Continued)

(56) References Cited

U.S. PATENT DOCUMENTS 6,102,950 A * 8/2000 Vaccaro ................ A61F 2/4637
606/247
7,896,919 B2 * 3/2011 Belliard ................ A61F 2/4425
623/17.15

(Continued)

*Primary Examiner* — Jessica Weiss
(74) *Attorney, Agent, or Firm* — LIU & LIU

(57) ABSTRACT

A kit of parts from which selection is made to form an intervertebral fusion device. The kit of parts comprises a plurality of different endplates and a core component. Each of the plurality of different endplates is configured to be received in an intervertebral space defined between first and second vertebrae. The core component is configured to engage with each of the plurality of endplates and a selected one of the plurality of endplates when the selected endplate and the core component are received in the intervertebral space. Each of the plurality of endplates defines a bone graft aperture which is open at top and bottom surfaces of the endplate and extends between the top and bottom surfaces, the thus defined bone graft apertures being of substantially the same dimensions as one another when the plurality of endplates are in plan view. The core component defines a bone graft material holding space having a holding space opening in one of a core component top surface and a core component bottom surface of the core component. The holding space opening is of substantially the same dimensions as each of the bone graft apertures when the core component is in plan view. The holding space opening is substantially coextensive with the bone graft aperture of the selected endplate in plan view and when the core component is engaged with and in registration with the selected endplate.

23 Claims, 16 Drawing Sheets

Related U.S. Application Data

12, 2020, now Pat. No. 12,127,952, application No. 18/928,707 is a continuation-in-part of application No. 17/841,648, filed on Jun. 15, 2022, now abandoned, which is a continuation-in-part of application No. 17/294,683, filed as application No. PCT/GB2019/053275 on Nov. 19, 2019, now Pat. No. 12,090,062.

(58) Field of Classification Search
USPC ............................................ 623/17.11–17.16
See application file for complete search history.

(56) References Cited

U.S. PATENT DOCUMENTS 10,278,830 B1 * 5/2019 Walker .................. A61F 2/4455
2004/0143332 A1 * 7/2004 Krueger ............. A61B 17/1604 606/90
2004/0254644 A1 * 12/2004 Taylor ................... A61F 2/4425 623/17.13
2007/0185578 A1 * 8/2007 O’Neil .................. A61F 2/4425 623/17.14
2007/0270957 A1 * 11/2007 Heinz ................... A61F 2/4465 623/17.11
2008/0294260 A1 * 11/2008 Gray .................. A61B 17/8047 623/17.15
2012/0232552 A1 * 9/2012 Morgenstern Lopez .................... A61B 17/3439 606/45
2013/0006357 A1 * 1/2013 Krueger .................... A61F 2/44 623/17.13
2013/0060336 A1 * 3/2013 Hooper ................... A61F 2/447 623/17.11
2015/0320568 A1 * 11/2015 Ameil ................... A61F 2/4455 623/17.13

* cited by examiner

INTERVERTEBRAL DEVICES

This application is a continuation-in-part of: (a) U.S. patent application Ser. No. 17/430,711 filed on Aug. 12, 2021, issuing as U.S. Pat. No. 12,127,952 on Oct. 29, 2024, which is a 371 of International Application No. PCT/GB2020/050328 filed on Feb. 12, 2020, which claims priority of GB Patent Application No. 1902002.3 filed on Feb. 13, 2019; and (b) U.S. patent application Ser. No. 17/841,648 filed on Jun. 15, 2022, which is a continuation-in-part of U.S. patent application Ser. No. 17/294,683 filed on May 17, 2021, issued as U.S. Pat. No. 12,090,062 on Sep. 17, 2024, which is a 371 of International Application No. PCT/GB2019/053275 filed on Nov. 19, 2019, which claims priority of GB Patent Application No. 1818849.0 filed on Nov. 19, 2018. These applications are fully incorporated by reference as if fully set forth herein.

FIELD OF THE INVENTION

The present invention relates to intervertebral devices and more specifically to intervertebral fusion devices.

BACKGROUND ART

Adjacent vertebrae in the spinal column are coupled to each other by an intervertebral disc. The intervertebral disc holds the adjacent vertebrae together and functions as a cushion between the vertebrae whilst allowing for relative movement of the vertebrae. Problems with intervertebral discs arise from one or more of a range of diseases and conditions. A surgical procedure, such as spinal fusion, may be used to address such problems. A typical spinal fusion procedure involves partial or full removal of a problematic intervertebral disc and installation of an intervertebral device in the place of the partially or fully removed intervertebral disc.

Known intervertebral devices are of varied form and function. Many known intervertebral devices are configured to provide for adjustment of height and functional spine unit angle to address differing extents of removal of an intervertebral disc, differing anatomy and spinal deformity. Furthermore, ease of assembly, installation, including reduced impaction loads during insertion, and disassembly are design objects for known intervertebral devices aside from issues of manufacturability and cost. Some known intervertebral devices are characterised by their complexity with such complexity being liable to result in compromise on ease of assembly, installation and disassembly, in compromise on long-term reliability, or in risk to the patient, such as from wear of material from the intervertebral device over time and loss of spinal correction.

The present inventors have become appreciative of shortcomings of known intervertebral devices, such as the shortcomings mentioned above. The present invention has been devised in light of the inventors' appreciation of such shortcomings. It is therefore an object for the present invention to provide an improved intervertebral device and more specifically an improved intervertebral fusion device. It is a further object for the present invention to provide an improved method of installing an intervertebral device in an intervertebral space between first and second adjacent vertebrae and more specifically an improved method of installing an intervertebral fusion device.

STATEMENT OF INVENTION

According to a first aspect of the present invention there is provided a kit of parts from which selection is made to form an intervertebral fusion device, the kit of parts comprising:

- a plurality of different endplates each of which is configured to be received in an intervertebral space defined between first and second vertebrae; and
- a core component configured to engage with each of the plurality of endplates and a selected one of the plurality of endplates when the selected endplate and the core component are received in the intervertebral space, wherein
- each of the plurality of endplates defines a bone graft aperture which is open at top and bottom surfaces of the endplate and extends between the top and bottom surfaces, the thus defined bone graft apertures being of substantially the same dimensions as one another when the plurality of endplates are in plan view,
- the core component defines a bone graft material holding space having a holding space opening in one of a core component top surface and a core component bottom surface of the core component,
- when the core component is in plan view the holding space opening is of substantially the same dimensions as each of the bone graft apertures, and
- the holding space opening is substantially coextensive with the bone graft aperture of the selected endplate in plan view and when the core component is engaged with and in registration with the selected endplate.

The kit of parts comprises a plurality of different endplates and a core component. The plurality of different endplates may consist of at least two endplates. The plurality of endplates may differ from one another in respect of at least one of material composition, such as a coating thereon, configuration, such as in respect of coronal slope, and dimensions, such as length in the anterior-posterior direction and/or width in the transverse direction, and as described further below. Each of the plurality of endplates is configured to be received in an intervertebral space defined between first and second vertebrae.

The core component is configured to engage with each of the plurality of endplates and a selected one of the plurality of endplates when the selected endplate and the core component are received in the intervertebral space. The clinician may select for use one of the plurality of endplates in dependence on the patent's requirements.

Each of the plurality of endplates defines a bone graft aperture which is open at top and bottom surfaces of the endplate and extends between the top and bottom surfaces. The thus defined bone graft apertures are of substantially the same dimensions as one another when the plurality of endplates are in plan view, Plan view as mentioned herein may mean viewing from a direction which is orthogonal to a direction of insertion of the intervertebral fusion device into the intervertebral space and orthogonal to a transverse direction of the intervertebral fusion device. Plan view as mentioned herein may mean, according to a different perspective, viewing in the spinal direction, i.e. the direction of separation of the first and second vertebrae from each other.

The core component defines a bone graft material holding space having a holding space opening in one of a core component top surface and a core component bottom surface of the core component. In use, the bone graft material holding space may be packed with bone graft material before the core component is brought into engagement with the selected endplate. More preferably, bone graft material may be injected into the bone graft material holding space when the intervertebral fusion device is installed in the intervertebral space.

When the core component is in plan view the holding space opening is of substantially the same dimensions as each of the bone graft apertures. Furthermore, the holding space opening is substantially coextensive with the bone graft aperture of the selected endplate in plan view and when the core component is engaged with and in registration with the selected endplate. Having a holding space opening which is substantially coextensive with the bone graft aperture of the selected endplate may provide for ease of movement of bone graft material from the holding space opening into the bone graft aperture. Aside from this, having a holding space opening which is substantially coextensive with the bone graft aperture of the selected endplate and around substantially all of the holding space opening may provide for more even distribution of migrated bone graft material across the bone graft aperture and compared with coextensivity around only part of the holding space opening. Furthermore, having bone graft apertures of substantially the same dimensions as one another when the plurality of endplates are in plan view means that the aforementioned advantages may be obtained regardless of which one of the plurality of endplates is selected for formation of the intervertebral fusion device.

The plurality of different endplates may be a plurality of different superior endplates and the holding space opening may be in the core component top surface. When the superior endplate is brought into engagement with the core component, the core component top surface may face the bottom surface of the selected superior endplate. In use, bone graft material may migrate from the bone graft material holding space through the holding space opening and into the bone graft aperture of the superior endplate.

Alternatively or in addition, the plurality of different endplates may be a plurality of different inferior endplates and the holding space opening may be in the core component bottom surface. When the inferior endplate is brought into engagement with the core component, the core component bottom surface may face the top surface of the selected inferior endplate. In use, bone graft material may migrate from the bone graft material holding space through the holding space opening and into the bone graft aperture of the inferior endplate.

When formed, the intervertebral fusion device may have the core component and only one endplate whereby the intervertebral fusion device is a two component device. Alternatively, and in forms which are preferred in certain applications, the intervertebral fusion device may have the core component and two endplates, i.e. a superior endplate and an inferior endplate, whereby the intervertebral fusion device is a three component device. Furthermore, the bone graft material holding space may have two holding space openings, i.e. a first holding space opening in the core component top surface and a second holding space opening in the core component bottom surface. Bone graft material may therefore migrate from the bone graft material holding space to the bone graft aperture in each of the superior and inferior endplates.

The kit of parts may comprise plural different core components, each of the plural core components defining a bone graft material holding space having a holding space opening in one of a core component top surface and a core component bottom surface of the core component. Furthermore, the plural holding space openings may be of substantially the same dimensions as one another when the plurality of core components are in plan view. The intervertebral fusion device May comprise a selected one of the plural different core components with selection depending on the patient's requirements. The plurality of core components may differ from one another in respect of at least one of material composition, configuration, such as in respect of lordotic angle, and dimensions, such as height, and as described further below. The plurality of different core components may consist of at least two core components.

Having plural holding space openings of substantially the same dimensions as one another may provide for ease of movement of bone graft material from the holding space opening into the bone graft aperture regardless of which one of the plural core components is selected to form the intervertebral fusion device.

The core component may be configured and each of the plural endplates may be configured for inter-engagement of the core component and each endplate with each other. The core component may be configured and each of the plural endplates may be configured to prevent movement apart of core component and endplate in a direction orthogonal to a direction of insertion of the intervertebral fusion device into the intervertebral space and orthogonal to the transverse direction. Furthermore, the core component may be configured and each of the plural endplates may be configured to prevent relative movement of core component and endplate relative to each other in the transverse direction. The core component and endplate may be configured for relative sliding movement, such as by way of a tongue and groove arrangement as described further below. The core component may, for example, be brought into inter-engagement with the endplate before being moved slidably relative to the endplate to bring the core component and endplate into registration with each other.

The same features of the core component that provide for inter-engagement with one endplate may provide for inter-engagement with each of the other endplates. Each of the endplates may therefore comprise features for inter-engagement with the core component with such inter-engaging features corresponding from endplate to endplate. Such inter-engaging features may correspond in respect of shape and/or dimension and/or relative position of inter-engaging features.

The core component and each endplate may be configured to lock together when they are in registration with each other. The core component and each endplate may be configured to lock together to prevent movement in at least one of a direction opposite the direction of insertion of the intervertebral fusion device, the transverse direction and the direction of separation of the first and second vertebrae. Where the core component and each endplate are configured for relative sliding movement, locking together may comprise prevention of movement in the direction opposite the direction of insertion of the intervertebral fusion device into the intervertebral space. Locking may be by way of one or more of the arrangements described below.

The same features of the core component that provide for locking with one endplate may provide for locking with each of the other endplates. Each of the endplates may therefore comprise features for locking with the core component with such locking features corresponding from endplate to endplate. Such locking features may correspond in respect of shape and/or dimension and/or relative position of locking features.

The bone graft material holding space may be defined by walls on at least three of four sides. A fourth side of the bone graft material holding space may be open at least in part to define a bone graft port whereby bone graft material may be injected into the bone graft material holding space, such as when the intervertebral fusion device is in the intervertebral space. A wall of the fourth side, and more specifically a wall defining the bone graft material holding space in part, and which defines the bone graft port may lie in a plane which is orthogonal to a direction of insertion of the core component into the intervertebral space.

The intervertebral fusion device formed from the kit of parts may be an anterior, anterior oblique, lateral or direct lateral intervertebral fusion device.

When clinicians are installing anterior lumbar interbody fusion (ALIF) devices and oblique lumbar interbody fusion (OLIF) devices they often determine clinical requirements, such as in respect of device height and lordotic angle, with reference to measurement from a datum towards the anterior aspect of the core component and endplate and when the core component and endplate are in registration with each other. This is because the clinician has sight of the anterior aspect of the core component and endplate when the device is in the intervertebral space.

In view of this, the core component and each of the plural different endplates may be configured such that a first surface on an outer surface of the core component towards the anterior aspect of the core component is adjacent or aligned with a second surface on an outer surface of each of the endplates towards their anterior aspects and when the core component is in registration with the endplate to thereby provide the datum. The core component may be in registration with the endplate when the core component and endplate are locked together as described elsewhere herein. There may therefore be adjacency or alignment of first and second surfaces regardless of which of the plural different endplates has been selected. For example, the first surface may be at a corner of the core component or may be a face of the core component between two corners. For example, the second surface may be at a corner of each of the endplates or may be a face of each endplate between two corners. The first and second surfaces may be located on their respective components such that their adjacency or alignment can be confirmed, such as visually, and measurements made from the adjacent or aligned first and second surfaces, i.e. from the anterior aspect.

As mentioned above, the plurality of endplates may differ from each other, such as in respect of coronal slope and dimensions, for example length in the anterior-posterior direction and/or width in the transverse direction. Regardless of differences from endplate to endplate, the plural different endplates may be configured such that their second locations are adjacent or align with the first location when the core component and endplate are in registration.

The clinician can often only achieve proper decompression of adjacent nerves if there is measurement from the posterior aspect of the core component and endplate and in particular when the device is for correcting lordosis. In light of this appreciation, the present inventors have devised a configuration of intervertebral fusion device, which comprises a core component and an endplate selected from a plurality of different endplates, to provide for ease of measurement from the posterior aspect of the intervertebral fusion device. The devised configuration may be particularly but not exclusively advantageous for ALIF and OLIF devices.

The core component and each of the plural different endplates may be configured such that a first surface on an outer surface of the core component towards the posterior aspect of the core component is adjacent or aligned with a second surface on an outer surface of each of the endplates towards their posterior aspects and when the core component is in registration with the endplate to thereby provide the datum. The core component may be in registration with the endplate when the core component and endplate are locked together as described elsewhere herein. There may therefore be adjacency or alignment of first and second surfaces regardless of which of the plural different endplates has been selected. For example, the first surface may be at a corner of the core component or may be a face of the core component between two corners. For example, the second surface may be at a corner of each of the endplates or may be a face of each endplate between two corners. The first and second surfaces may be located on their respective components such that their adjacency or alignment can be confirmed, such as visually or by way x-ray inspection, and measurements made from the adjacent or aligned first and second surfaces.

Adjacency or alignment of the first location and the second location may take place outside the intervertebral space and determinations concerning measurements may be made by the clinician before the intervertebral fusion device is installed in the intervertebral space. Alternatively or in addition, adjacency or alignment of the first location and the second location may take place in the intervertebral space and determinations based on measurements may be made by the clinician when the intervertebral fusion device is in the intervertebral space. More specifically, the clinician may take measurements by way of the like of x-ray inspection in view of the posterior aspect not being observable and make his or her determinations based on such measurements.

Further embodiments of the first aspect of the present invention may comprise one or more features of any of the aspects of the invention described below.

According to a second aspect of the present invention, there is provided a method of installing an intervertebral fusion device in an intervertebral space between first and second adjacent vertebrae, the method comprising:

- selecting one of a plurality of different endplates comprised in a kit of parts, each of the plurality of endplates configured to be received in an intervertebral space defined between first and second vertebrae, and each of the plurality of endplates defining a bone graft aperture which is open at top and bottom surfaces of the endplate and extends between the top and bottom surfaces, the thus defined bone graft apertures being of substantially the same dimensions as one another when the plurality of endplates are in plan view;
- engaging a core component comprised in the kit of parts with the selected endplate to form an intervertebral fusion device, the core component configured to engage with each of the plurality of endplates, the core component defining a bone graft material holding space having a holding space opening in one of a core component top surface and a core component bottom surface of the core component; and
- installing the intervertebral fusion device in the intervertebral space and such that the core component is engaged with the selected endplate when in the intervertebral space, wherein when the core component is in plan view the holding space opening is of substantially the same dimensions as each of the bone graft apertures, and the holding space opening is substantially coextensive with the bone graft aperture of the selected endplate in plan view and when the core component is engaged with and in registration with the selected endplate.

The core component and the selected endplate may be brought into engagement with each other outside of the intervertebral space and before the thus formed intervertebral fusion device is installed in the intervertebral space. Alternatively, one of the core component and the selected endplate, and more usually the selected endplate, is installed in intervertebral space and then the other of the core component and the selected endplate is installed in the intervertebral space and such that the core component and the selected endplate are brought into engagement with each other to form the intervertebral fusion device in situ in the intervertebral space.

Further embodiments of the second aspect of the present invention may comprise one or more features of the first aspect of the present invention.

As described above, the same features of the core component that provide for inter-engagement with one endplate may provide for inter-engagement with each of the other endplates whereby each of the endplates comprises features for inter-engagement with the core component with such inter-engaging features corresponding from endplate to endplate. The inventors have appreciated these features to be of wider applicability than hitherto described. Therefore, and according to a third aspect of the present invention, there is provided a kit of parts from which selection is made to form an intervertebral fusion device, the kit of parts comprising:

a plurality of different endplates each of which is configured to be received in an intervertebral space defined between first and second vertebrae; and a core component configured to inter-engage with each of the plurality of endplates and a selected one of the plurality of endplates when the selected endplate and the core component are received in the intervertebral space, wherein each of the plurality of endplates defines a bone graft aperture, the core component defines a bone graft material holding space having a holding space opening in one of a core component top surface and a core component bottom surface of the core component, the core component comprises core component features which inter-engage with endplate features of each of the plural endplates whereby the core component inter-engages with the endplate, the endplate features corresponding from endplate to endplate of the plurality of endplates, and the holding space opening is in registration with the bone graft aperture of the selected endplate regardless of which of the plurality of endplates is selected and when the core component is moved to its furthest extent in the anterior to posterior direction relative to the selected endplate and when the core component is inter-engaged with the selected endplate.

The holding space opening may be substantially coextensive with the bone graft aperture of the selected endplate in plan view and when the core component is inter-engaged with the selected endplate and when the core component is moved to its furthest extent in the anterior to posterior direction relative to the selected endplate.

Further features of the third aspect of the present invention may comprise one or more features of the first aspect of the present invention.

According to a first further aspect of the present invention there is provided an intervertebral fusion device comprising:

a superior component having a superior component top side and a superior component bottom side, the superior component configured to be received in an intervertebral space between first and second vertebrae whereby the superior component top side abuts against the first vertebra;

an inferior component having an inferior component top side and an inferior component bottom side, the inferior component configured to be received in the intervertebral space between the first and second vertebrae whereby the inferior component bottom side abuts against the second vertebra, the superior component bottom side and the inferior component top side opposing each other when the superior and inferior components are received in the intervertebral space;

a core component configured for insertion between the superior and inferior components whereby a separation between the superior and inferior components and hence height of the intervertebral fusion device are determined when the intervertebral fusion device is in the intervertebral space, wherein each of the superior component top side and the inferior component bottom side is one of: oblong having a major axis; and square, being bounded by four edges, and wherein the core component comprises a first core profile and a second core profile, the superior component bottom side comprises a superior component profile, the inferior component top side comprises an inferior component profile, the first core profile cooperating with the superior component profile and the second core profile cooperating with the inferior component profile during insertion of the core component between the superior and inferior components whereby the core component moves in a direction oblique to the major axis where the superior component top side or the inferior component bottom side is oblong or to an edge of the superior component top side or the inferior component bottom side where the superior component top side or the inferior component bottom side is square.

The intervertebral fusion device comprises three main components, namely a superior component, an inferior component and a core component. In use, the superior and inferior components are placed in an intervertebral space between first and second vertebrae formed by at least partial removal of a problematic intervertebral disc. The superior component has a superior component top side and a superior component bottom side with the superior component placed in the intervertebral space such that the superior component top side faces the first vertebra or what might remain of a partially removed intervertebral disc. The inferior component has an inferior component top side and an inferior component bottom side with the inferior component placed in the intervertebral space such that the inferior component bottom side faces the second vertebra or what might remain of a partially removed intervertebral disc. The superior component bottom side and the inferior component top side oppose each other when the superior and inferior components are received in the intervertebral space. The superior and inferior components may be in registration with each other when in the intervertebral space and more specifically when the core component is fully inserted between the superior and inferior components, as described below.

The core component is configured for insertion between the superior and inferior components. Upon insertion the core component determines a separation between the superior and inferior components and hence a height of the intervertebral fusion device with the superior component top side abutting against the first vertebra or what remains of the partially removed intervertebral disc and with the inferior component bottom side abutting against the second vertebra or what remains of the partially removed intervertebral disc. Differing heights of intervertebral fusion device may be provided by selection from plural core components of different height.

Each of the superior component top side and the inferior component bottom side is one of oblong and square. The superior component top side and the inferior component bottom side may be substantially the same shape and, more specifically, of substantially the same dimensions. Where the superior component top side and the inferior component bottom side are oblong, each of the superior component top side and the inferior component bottom side may be an oblong rectangle and more specifically a rectangle with rounded corners. Alternatively, each of the superior component top side and the inferior component bottom side may be an oblong rectangle in which each of two corners at opposite ends of a long edge of the rectangle is rounded with the other two corners not being rounded. Each of the superior component top side and the inferior component bottom side may therefore be 'D' shaped. Where the superior component top side and the inferior component bottom side are square, two corners on a same edge of the square only of the four corners of the square may be rounded or all four corners of the square may be rounded.

Each of the superior component top side and the inferior component bottom side has a major axis (i.e. a line that passes through the center of each short side of the superior component top side or the inferior component bottom side) when they are oblong whereby the superior component top side and the inferior component bottom side are wider than deep. Alternatively, the superior component top side and the inferior component bottom side are square, the square being bounded by four edges, whereby the width and depth of each of the superior component top side and the inferior component bottom side are the same.

The core component comprises a first core profile and a second core profile. The superior component bottom side comprises a superior component profile and the inferior component top side comprises an inferior component profile. The first core profile cooperates with the superior component profile and the second core profile cooperates with the inferior component profile during insertion of the core component between the superior and inferior components whereby the core component moves in a direction oblique to the major axis where the superior component top side or the inferior component bottom side is oblong or to an edge of the superior component top side or the inferior component bottom side where the superior component top side or the inferior component bottom side is square.

The intervertebral fusion device is brought into use by inserting the superior and inferior components into the intervertebral space, as described above, and without the core component. Introduction of the superior and inferior components without the core component into the intervertebral space reduces height allowing for ease of introduction and with reduced requirement for retraction of the adjacent blood vessels. Risk of damage to the adjacent blood vessels is therefore reduced. Having a superior component, an inferior component and a core component according to the invention provides improved scope for introduction of intervertebral fusion devices of larger footprint, and hence increased vertebra contact area, and also for introduction of intervertebral fusion devices which provide greater correction angles.

Having an oblong shape for the superior component top side and the inferior component bottom side means the superior component top side and the inferior component bottom side are wider than deep whereby they are more likely to conform to the shape and size of the intervertebral space than a narrow, square or circular superior component top side and inferior component bottom side. Conformance to the shape and size of the intervertebral space means the interbody fusion device is more likely to be situated over a greater extent of strong bone towards the periphery of the vertebrae defining the intervertebral space. There may therefore be reduced risk of the interbody fusion device subsiding into vertebrae after surgery. The superior and inferior components may thus confer the benefit of anteriorly inserted interbody fusion devices.

When the superior and inferior components have been positioned appropriately in the intervertebral space, the core component is inserted between the superior and inferior components. The profiles of the core component, the superior component bottom side and the inferior component top side cooperate to determine the direction of insertion such that it is oblique to the major axis of the superior component top side and the inferior component bottom side where the superior component top side and the inferior component bottom side are oblong or such that the direction of insertion is oblique to an edge of the superior component top side and the inferior component bottom side where the superior component top side and the inferior component bottom side are square. Oblique insertion of the core components, and typically with an inserter, presents a reduced risk of damage to adjacent blood vessels. Furthermore, the intervertebral fusion device is raised to a desired height by insertion of the core component in the intervertebral space thereby presenting less risk of damage than insertion of an already full height intervertebral fusion device into the intervertebral space. In addition, assembly of the intervertebral fusion device in-situ improves scope for deformity correction through selection from a range of core components providing for different extents of correction angle.

As described above, each of the superior component top side and the inferior component bottom side has a major axis whereby the superior component top side and the inferior component bottom side are wider than deep. The superior component top side and the inferior component bottom side are therefore of greater extent in the transverse direction than in the orthogonal anatomical posterior to anterior direction. Alternatively, each of the superior component top side and the inferior component bottom side is square whereby the width and depth of each of the superior component top side and the inferior component bottom side are the same.

The profiles of the core component, the superior component bottom side and the inferior component top side may cooperate to determine the direction of insertion such that it is at least 10, 20, 30, 40, 50, 60, 70 or 80 degrees to the major axis or to the edge. The direction of insertion may be 45 degrees to the major axis or edge. Where each of the superior component top side and the inferior component bottom side is an oblong rectangle, the profiles may be located on their respective components such that the core component is inserted at a corner of the oblong rectangle.

The superior component top side and the inferior component bottom side may be of substantially the same extent. The profiles may be located on their respective components such that the superior and inferior components have the same orientation and such that the superior component top side and the inferior component bottom side are in registration with each other during insertion of the core component between the superior and inferior components.

Having a core component of smaller extent than each of the superior and inferior components may provide for ease of in-situ insertion of the core component between the superior and inferior components with reduced risk of damage to adjacent blood vessels. The core component may have a core component top side and a core component bottom side, the core component top side facing the superior component bottom side and the core component bottom side facing the inferior component top side when the core component is received between the superior and inferior components. Each of the core component top side and the core component bottom side may extend over an area that is at least 5%, 10%, 15% or 20% smaller and more specifically 25% smaller than an area of each of the superior component bottom side and the inferior component top side.

Where the superior component top side and the inferior component bottom side are oblong rectangles and when the core component is received between the superior and inferior components, each of the superior component top side and the inferior component bottom side may extend beyond the core component. The core component may therefore be narrower than each of the superior and inferior components whereby the core component is more readily received in the intervertebral space with reduced likelihood of damage to adjacent blood vessels. Each of the superior component top side and the inferior component bottom side may extend beyond the core component towards each of a first pair of diagonally opposite corners of the superior component top side and the inferior component bottom side. More specifically, each of the superior component top side and the inferior component bottom side may not extend beyond or may extend to substantially a same extent as the core component at at least one of a second pair of diagonally opposite corners of the superior component top side and the inferior component bottom side. The direction of insertion of the core component as determined by the cooperating surface profiles may extend between the corners in the second pair of pair of diagonally opposite corners.

As described above, the first core profile cooperates with the superior component profile and the second core profile cooperates with the inferior component profile during insertion of the core component between the superior and inferior components whereby the core component moves in a direction oblique to the major axis or to the edge. The superior component profile may comprise a first superior component formation and a second superior component formation, the first and second superior component formations spaced apart from each other. The core component may be received between the first and second superior component formations during insertion. The first and second superior component formations may therefore oppose each other with the first and second superior component formations defining a track along which the core component moves during insertion. The track may be linear or curvilinear.

The core component may have first and second lateral sides which face in opposite directions and which each face in a direction orthogonal to a direction of insertion of the core component and to a direction of separation of the inferior and superior components. A first superior core formation may be on the first lateral side and a second superior core formation may be on the second lateral side. The first superior component formation and the first superior core formation may cooperate and the second superior component formation and the second superior core formation may cooperate to limit movement of the core component relative to the superior component in a direction orthogonal to the direction of insertion while the core component is being inserted. More specifically, the superior component formations and the superior core formations may provide a snug fit for the core component in the orthogonal direction. The first superior component formation and the first superior core formation may therefore abut and the second superior component formation and the second superior core formation may abut whilst allowing for movement of the core component relative to the superior component. The superior component formations and the superior core formations may be of corresponding shape and more specifically one of linear and curved depending on whether the track along which the core component moves is linear or curvilinear.

The inferior component profile may comprise a first inferior component formation and a second inferior component formation, the first and second inferior component formations spaced apart from each other. The core component may be received between the first and second inferior component formations during insertion. The first and second inferior component formations may therefore oppose each other with the first and second inferior component formations defining a track and more specifically a linear or curvilinear track along which the core component moves during insertion. A first inferior core formation may be on the first lateral side of the core component and a second inferior core formation may be on the second lateral side of the core component. The first inferior component formation and the first inferior core formation may cooperate and the second inferior component formation and the second inferior core formation may cooperate to limit movement of the core component relative to the inferior component in a direction orthogonal to the direction of insertion while the core component is being inserted. More specifically, the inferior component formations and the inferior core formations may provide a snug fit for the core component in the orthogonal direction. The first inferior component formation and the first inferior core formation may therefore abut and the second inferior component formation and the second inferior core formation may abut whilst allowing for movement of the core component relative to the inferior component. The inferior component formations and the inferior core formations may be of corresponding shape and more specifically one of linear and curved depending on whether the track along which the core component moves is linear or curvilinear.

The first superior core formation and the first inferior core formation may be spaced apart on the first lateral side of the core component in a direction of separation of the superior and inferior components. The second superior core formation and the second inferior core formation may be spaced apart on the second lateral side of the core component in a direction of separation of the superior and inferior components.

The core component top side and the core component bottom side may be inclined to each other. The core component may therefore have the form of a wedge. The core component top side and the core component bottom side may not meet at an acute angle whereby the core component has the form of a frustum of a wedge. The core component and the inferior and superior components may be configured for insertion of the core component to be led by the thinner edge of the thinner and thicker edges of the core component. An inclination of the inferior and superior components relative to each other may thus be determined by way of the core component further to a separation between the inferior and superior components. Extent of inclination of the inferior and superior components may be determined by selection from a plurality of core components having top and bottom sides of different relative inclinations. Alternatively or in addition, at least one of the inferior and superior components may be wedge shaped to provide for inclination of the core component top side and the core component bottom side in relation to each other.

A leading edge of the core component, for example the thinner edge when the core component is wedge shaped, may have at least one rounded corner. Such a radius on a corner of the leading edge may provide for ease of insertion of the core component between the inferior and superior components and also ease of separation of adjacent blood vessels with reduced risk of damage to the adjacent blood vessels.

The superior component, the inferior component and the core component may be separate components. Furthermore, the superior component and the inferior component may be disconnected from each other in the absence of the core component. Having separate inferior and superior components and core component and more specifically disconnected inferior and superior components means that the components may be introduced to the intervertebral space more gently compared with known single piece intervertebral fusion devices which often need to be hammered into place. A less gentle insertion process may damage the intervertebral fusion device, may increase time required for the intervertebral fusion device to settle in the intervertebral space, and may result in trauma to vertebral bodies or adjacent soft tissues including neural structures. On the subject of trauma, a device that is hammered into place is liable to create microfractures in the vertebrae which could lead to subsidence of the device into the host bone. Furthermore, having separate components and in particular a core component separate to the inferior and superior components allows for differences in dimensions of intervertebral spaces, differences in angle between the adjacent vertebrae that define the intervertebral space, and differences in degree of spinal alignment and/or correction.

Each of the superior component, the inferior component and the core component may be integrally formed. The superior component and the inferior component may not be attached to each other, other than by way of the core component.

Each of the inferior and superior components may have the form of a plate, albeit a plate having structures thereon that provide for mechanical engagement with the core component, whereby it is thin relative to its width and depth. At least one of the superior component top side and the inferior component bottom side may be shaped in the coronal or sagittal planes, for example domed, to enhance fit and contact with adjacent vertebrae. The coronal plane divides the body into dorsal and ventral (back and front, or posterior and anterior) portions. A direction may be said to be coronal if it lies on or is parallel to the coronal plane. A coronal direction may thus extend from one of the right and left of the body to the other of the right and left of the body.

At least one of the superior component top side and the inferior component bottom side may be configured to provide for fusion. For example, the top or bottom side may comprise formations, such as protrusions, which, in use, engage with the bone of the vertebra. By way of another example, the top and/or bottom side may define apertures for passage of bone graft material therethrough from an interior of the intervertebral fusion device. By way of a further example, the top or bottom side may have a coating thereon or impregnation therein. The coating or impregnation may comprise material that provides for bone adhesion and/or bone formation to encourage bone to grow up to and bond onto the intervertebral fusion device to thereby provide long term stable attachment. One or more known coatings may be used, such as porous mesh, tricalcium phosphate (TCP), hydroxyapatite (HA) or bone morphogenetic protein (BMP).

At least one of the superior component, the core component and the inferior component may be formed from a metal, such as titanium, or a metal alloy, such as stainless steel, Ti6Al4V, CoCr or nitinol. Nitinol may be useful in respect of cooperating parts of the superior component, the core component and the inferior component. At least one of the superior component, the core component and the inferior component may be formed from a plastics material and more specifically a thermoplastic polymer, such as PEEK or carbon reinforced PEEK. In forms of the invention, the core component may be formed by 3D printing whereby the core component has the form of a 3D lattice. The aforementioned materials may be used to form the core component by way of 3D printing.

Each of the superior component top side and the inferior component bottom side may have a width of between 24 mm and 44 mm and a depth of between 20 mm and 32 mm. Where the superior component top side and the inferior component bottom side are oblong, a ratio of width to depth may be between 1.15 to 2.

The core component may have a width of between 20 mm and 40 mm and a depth of between 10 mm and 25 mm.

When assembled, i.e. when the core component is fully received between the superior and inferior components, the intervertebral fusion device may have a height between 5 mm and 12 mm. The height may be measured at the back of the intervertebral fusion device, i.e. the part of the intervertebral fusion device first received in the intervertebral space upon insertion. The intervertebral fusion device may have a corrective angle of between 0 degrees and 30 degrees.

According to a second further aspect of the present invention there is provided a method of installing an intervertebral fusion device in an intervertebral space between first and second adjacent vertebrae, the intervertebral fusion device comprising a superior component having a superior component top side and a superior component bottom side, an inferior component having an inferior component top side and an inferior component bottom side, and a core component, the method comprising:

- positioning the superior component and the inferior component relative to each other in the intervertebral space such that the superior component bottom side and the inferior component top side oppose each other; and
- inserting the core component between the superior and inferior components whereby a separation between the superior and inferior components is determined and the superior component top side abuts against the first vertebra and the inferior component bottom side abuts against the second vertebra, wherein each of the superior component top side and the inferior component bottom side is one of: oblong having a major axis; and square, being bounded by four edges, and wherein the core component comprises a first core profile and a second core profile, the superior component bottom side comprises a superior component profile, the inferior component top side comprises an inferior component profile, the first core profile cooperating with the superior component profile and the second core profile cooperating with the inferior component profile during insertion of the core component between the superior and inferior components whereby the core component moves in a direction oblique to the major axis where the superior component top side or the inferior component bottom side is oblong or to an edge of the superior component top side or the inferior component bottom side where the superior component top side or the inferior component bottom side is square.

The intervertebral fusion device comprises a superior component having a superior component top side and a superior component bottom side, an inferior component having an inferior component top side and an inferior component bottom side, and a core component. The method of installing the intervertebral fusion device in an intervertebral space between first and second adjacent vertebrae comprises positioning the superior component and the inferior component relative to each other in the intervertebral space such that the superior component bottom side and the inferior component top side oppose each other. The superior component and the inferior component may be moved such that they have a desired orientation in the intervertebral space whereby there is no need for a change of orientation after the core component is inserted between the superior and inferior components. The method may therefore further comprise changing an orientation of the superior component and the inferior component in the intervertebral space. The core component is inserted between the superior and inferior components to determine a separation between the superior and inferior components and such that the superior component top side abuts against the first vertebra and the inferior component bottom side abuts against the second vertebra. The method may further comprise making no change in orientation of the intervertebral fusion device during or after insertion of the core component between the superior and inferior components.

Each of the superior component top side and the inferior component bottom side has a major axis (i.e. a line that passes through the center of each short side of the superior component top side or the inferior component bottom side) when they are oblong whereby the superior component top side and the inferior component bottom side are wider than deep. Alternatively, the superior component top side and the inferior component bottom side are square, the square being bounded by four edges, whereby the width and depth of each of the superior component top side and the inferior component bottom side are the same. Alternatively, the superior component top side and the inferior component bottom side may be of different shape, for example oblongs of different shape. By way of further example, one of the superior component top side and the inferior component bottom side may be square and the other of the superior component top side and the inferior component bottom side may be oblong.

The core component comprises a first core profile and a second core profile. The superior component bottom side comprises a superior component profile and the inferior component top side comprises an inferior component profile. The first core profile cooperates with the superior component profile and the second core profile cooperates with the inferior component profile during insertion of the core component between the superior and inferior components whereby the core component moves in a direction oblique to the major axis where the superior component top side or the inferior component bottom side is oblong or to an edge of the superior component top side or the inferior component bottom side where the superior component top side or the inferior component bottom side is square. Different superior and inferior components may be selected depending on patient anatomy.

Further embodiments of the second further aspect of the present invention may comprise one or more features of the first further aspect of the present invention.

According to a third further aspect of the present invention there is provided an intervertebral fusion device comprising:

a superior component having a superior component top side and a superior component bottom side, the superior component configured to be received in an intervertebral space between first and second vertebrae whereby the superior component top side abuts against the first vertebra;

an inferior component having an inferior component top side and an inferior component bottom side, the inferior component configured to be received in the intervertebral space between the first and second vertebrae whereby the inferior component bottom side abuts against the second vertebra, the superior component bottom side and the inferior component top side opposing each other when the superior and inferior components are received in the intervertebral space; and a core component configured for insertion between the superior and inferior components whereby a separation between the superior and inferior components is determined when the intervertebral fusion device is in the intervertebral space, wherein the core component comprises a first core formation and one of the inferior component top side and the superior component bottom side comprises a first component formation, the first core formation inter-engaging with the first component formation to present a barrier to separation of the core component and the corresponding one of the inferior and superior components from each other during insertion of the core component, the core component comprises a core profile and the other of the inferior component top side and the superior component bottom side comprises a component profile, the core profile and the component profile cooperating with each other during insertion of the core component to thereby guide the core component, there being no barrier to separation of the core component and the corresponding one of the inferior and superior components from each other during insertion of the core component, and the core component comprises a second core formation and the other of inferior component top side and the superior component bottom side comprises a second component formation, the second core formation inter-engaging with the second component formation to present a barrier to separation of the core component and the corresponding one of the inferior and superior components from each other when the core component is fully received between the inferior and superior components.

The intervertebral fusion device comprises three main components, namely a superior component, an inferior component and a core component. In use, the superior and inferior components are placed in an intervertebral space between first and second vertebrae formed by at least partial removal of a problematic intervertebral disc. The superior component has a superior component top side and a superior component bottom side with the superior component placed in the intervertebral space such that the superior component top side faces the first vertebra or what might remain of a partially removed intervertebral disc. The inferior component has an inferior component top side and an inferior component bottom side with the inferior component placed in the intervertebral space such that the inferior component bottom side faces the second vertebra or what might remain of a partially removed intervertebral disc. The superior component bottom side and the inferior component top side oppose each other when the superior and inferior components are received in the intervertebral space. The superior and inferior components may be in registration with each other when in the intervertebral space and more specifically when the core component is fully inserted between the superior and inferior components as described below.

The core component is configured for insertion between the superior and inferior components. In use, the core component may be inserted between the superior and inferior components when the superior and inferior components have been placed in the intervertebral space, as described above. Upon insertion the core component determines a separation between the superior and inferior components and hence a height of the intervertebral fusion device with the superior component top side abutting against the first vertebra or what remains of the partially removed intervertebral disc and with the inferior component bottom side abutting against the second vertebra or what remains of the partially removed intervertebral disc.

Differing heights of intervertebral fusion device may be provided by selection from plural core components of different height.

The core component comprises a first core formation and one of the inferior component top side and the superior component bottom side comprises a first component formation. The first core formation inter-engages with the first component formation to present a barrier to separation of the core component and the corresponding one of the inferior and superior components from each other during insertion of the core component. The barrier to separation may be presented in a separation direction that extends between the inferior and superior components. Inter-engagement of the first core formation with the first component formation may provide for and maintain proper relative location of the core component and the corresponding one of the inferior and superior components in the separation direction during insertion of the core component. An extent to which the corresponding one of the inferior and superior components may move away from the core component in the separation direction may thus be limited during insertion of the core.

The core component also comprises a core profile and the other of the inferior component top side and the superior component bottom side comprises a component profile. The core profile and the component profile cooperate with each other during insertion of the core component to thereby guide the core component. During insertion of the core component, there is no barrier to separation of the core component and the corresponding one of the inferior and superior components from each other. The lack of barrier means the corresponding one of the inferior and superior components may move away from and towards the core component during insertion of the core component. Allowing for such movement of the core component away from and towards the corresponding one of the inferior and superior components may provide for ease of initial insertion of the core component, such as by way of reduced insertion load, and may allow for the position of the corresponding one of the inferior and superior components to settle in relation to the core component as insertion progresses.

The core component also comprises a second core formation and the other of inferior component top side and the superior component bottom side comprises a second component formation. The second core formation inter-engages with the second component formation to present a barrier to separation of the core component and the corresponding one of the inferior and superior components from each other when the core component is fully received between the inferior and superior components. The corresponding one of the inferior and superior components and the core component are thus held in relation to each other when the core component is fully received between the inferior and superior components. The core component may be fully received between the inferior and superior components when the core component abuts against a posterior surface of at least one of the inferior and superior components. As described above, the core profile and the component profile may cooperate with each other during insertion of the core component to guide the core component. The lack of barrier allows for the position of the corresponding one of the inferior and superior components to settle in relation to the core component as insertion progresses. When the position of the corresponding one of the inferior and superior components has settled in relation to the core component and the core is fully inserted, the barrier presented by inter-engagement of the second core formation and the second component formation presents a barrier to separation of the core component and the corresponding one of the inferior and superior components from each other.

The first core formation may be an inferior core formation and the first component formation may be an inferior component formation comprised in the inferior component top side. The barrier to separation may therefore be presented in respect of the core component and the inferior component. Furthermore, the core profile may be a superior core profile and the component profile may be a superior component profile comprised in the superior component bottom side. The lack of barrier to separation may therefore be in respect of the core component and the superior component. Having the intervertebral fusion device configured in this fashion may mean that the inferior component and core component are held together by virtue of the barrier to separation to thereby provide a firm foundation on which the intervertebral fusion device is assembled by affording more freedom of movement to the superior component during insertion of the core component.

The core component may have an upper side and a lower side. When the core component is inserted between the inferior and superior components, the upper side may face the superior component bottom side and the lower side may face the inferior component top side. The upper side and the lower side of the core component may be inclined to each other. The core component may therefore have the form of a wedge. Having the superior component profile and the superior core profile cooperate with each other with there being no resistance to separation of the core component and the superior component from each other whilst the inferior core formation inter-engages with the inferior component formation allows a wedge-shaped core component to be inserted between the inferior and superior components.

The upper side and the lower side of the core component may not meet at an acute angle whereby the core component has the form of a frustum of a wedge. The core component and the inferior and superior components may be configured for insertion of the core component to be led by the thinner edge of the thinner and thicker edges of the core component. An inclination of the inferior and superior components relative to each other may thus be determined by way of the core component further to a separation between the inferior and superior components. Extent of inclination of the inferior and superior components may be determined by selection from a plurality of core components having upper and lower sides of different relative inclinations.

One of the inferior component formation and the inferior core formation may define a groove and the other of the inferior component formation and the inferior core formation may define an elongate protrusion, the elongate protrusion shaped to be slidably received in the groove. The elongate protrusion may be a friction fit in the groove. The groove and the elongate protrusion may extend between anterior and posterior aspects of the intervertebral fusion device. The inferior component formation may define the groove and the inferior core formation may define the elongate protrusion. Inter-engagement of groove and elongate protrusion present the barrier to separation as the core is inserted.

The inferior core formation may extend along the core component from a location on the core component spaced apart from an edge of the core component which leads insertion of the core component between the inferior and superior components. For example, and where the core component is wedge-shaped, the inferior core formation may extend along the core component from a location on the core component spaced apart from the thinner edge of the core component. Having the inferior core formation extend along the core component from a location on the core component spaced apart from the thinner edge allows the edge to be inserted first between the inferior and superior components and for the core component to be moved in the separation direction, i.e. the direction extending between the inferior and superior components, during a first stage of insertion before the inferior core formation and the inferior component formation inter-engage during a second stage of insertion. Allowing for freedom of movement in the separation direction during the first stage of insertion provides for ease of initial insertion of core component. For example, the edge of the core component may be inserted between the inferior and superior components with no great precision of positioning before the core component is pressed down against the inferior component as the core component is inserted further.

A leading edge of the core component, for example the thinner edge when the core component is wedge shaped, may have rounded corners. Such a radius on each corner of the leading edge may provide for ease of insertion of the core component between the inferior and superior components.

The inferior core formation may extend along the core component between the anterior and posterior aspects of the core component. Alternatively, the inferior core formation may extend along the core component for less than the span of the core component between the anterior and posterior aspects. The inferior core formation may extend along the core component starting from a location spaced apart from the leading edge of the core component by at least a quarter and more specifically at least a third of a distance between the leading edge and the opposite edge of the core component. In a particular form, the location may be spaced apart from the leading edge by about half of the distance between the leading edge and the opposite edge of the core component. The inferior core formation may extend along the core component from the starting location to the opposite edge of the core component.

The inferior component may comprise a first inferior component formation and a second inferior component formation, the first and second inferior component formations towards opposite edges of the inferior component and spaced apart in a direction transverse to the direction of insertion of the core component between the inferior and superior components. The core component may be received between the first and second inferior component formations during insertion. The first and second inferior component formations may therefore oppose each other. The core component may have first and second lateral sides which each face in a direction orthogonal to a direction of insertion of the core component and to a direction of separation of the inferior and superior components, with the first and second lateral sides facing in opposite directions. A first inferior core formation may be on the first lateral side and a second inferior core formation may be on the second lateral side. The first inferior component formation and the first inferior core formation may cooperate and the second inferior component formation and the second inferior core formation may cooperate to limit movement of the core component relative to the inferior component in the transverse direction. More specifically, the inferior component formations and the inferior core formations may provide a snug fit for the core component in the transverse direction.

The superior component may comprise a first superior component profile and a second superior component profile, the first and second superior component profiles towards opposite edges of the superior component and spaced apart in a direction transverse to the direction of insertion of the core component between the inferior and superior components. The core component may be received between the first and second superior component profiles during insertion. The first and second superior component profiles may therefore oppose each other. A first superior core profile may be on the first lateral side of the core component and a second superior core profile may be on the second lateral side of the core component. The first superior component profile and the first superior core profile may cooperate and the second superior component profile and the second superior core profile may cooperate to limit movement of the core component relative to the superior component in the transverse direction. More specifically, the superior component profiles and the superior core profiles may provide a snug fit for the core component in the transverse direction. As described above, there may be no barrier presented to separation of the superior component and the core component from each other. The superior component may therefore rise and fall in relation to the core component as insertion of the core component is guided by the superior component profiles and the superior core profiles.

The inferior component may comprise an inferior component rear formation which extends along a posterior aspect of the inferior component in a direction transverse to the direction of insertion of the core component. The posterior aspect is opposite the edge at which the core component is first received upon insertion. The core component may comprise an inferior core rear formation which extends along an edge of the core component which is first received between the inferior and superior components during insertion of the core component. The inferior component rear formation and the inferior core rear formation may inter-engage when the core component is fully received between the inferior and superior components to present a barrier to separation of the core component and the inferior component from each other in the separation direction. A leading edge of the core component, i.e. the edge first received between the inferior and superior components during insertion, may thus be secured against lifting away from the inferior component when the core component is fully inserted.

When the core component is fully inserted between the inferior and superior components it may be desirable to maintain the core component against ejection from between the inferior and superior components, i.e. movement of the core component in an opposite direction to the direction of insertion. The intervertebral fusion device may therefore comprise a locking arrangement, a first locking part comprised in the core component and a second locking part comprised in the inferior component, the first and second locking parts inter-engaging to present a barrier to ejection of the core component from between the inferior and superior components. The first locking part may comprise a living hinge which defines a protrusion thereon and the second locking part may define an aperture. The living hinge may be urged by inherent spring bias in a direction of separation of the inferior and superior components and such that that the protrusion on the living hinge is received in the aperture of the second locking part.

The second component formation may be a superior component rear formation comprised in the superior component. The superior component rear formation may extend along a posterior aspect of the superior component in a direction transverse to the direction of insertion of the core component. The posterior aspect is opposite the edge at which the core component is first received upon insertion. The second core formation may be a superior core rear formation comprised in the core component. The superior core rear formation may extend along an edge of the core component which is first received between the inferior and superior components during insertion of the core component. As described above in respect of the second component formation and the second core formation, the superior component rear formation and the superior core rear formation inter-engage when the core component is fully inserted to present a barrier to separation of the core component and superior component. As described above, the superior component profile and the superior core profile cooperate with each other to present no resistance to separation of the core component and the superior component from each other in the separation direction during insertion of the core component. The superior component rear formation and the superior core rear formation thus present a barrier to separation when the core component is fully inserted, for example when the core component abuts against a posterior surface of at least one of the inferior and superior components.

The superior component rear formation and the superior core rear formation may be configured such that they start to engage when the core component is at least 80% and more specifically at least 90% inserted between the inferior and superior components. The superior component rear formation and the superior core rear formation may be configured by their extension away from the posterior aspect towards the anterior aspect.

The superior component rear formation may comprise a first protrusion and the superior core rear formation may comprise a second protrusion, the second protrusion received on the core component side of the first protrusion when the core component is fully inserted. Furthermore, the superior component rear formation and the superior core rear formation may be shaped to draw the superior component and the core component progressively closer together during a last stage of insertion of the core component. As mentioned above, the superior component rear formation and the superior core rear formation may start to inter-engage when the core component is at least 80% inserted. Each of the first and second protrusions may define an inclined surface, the two inclined surfaces sliding over each other to draw the superior component and the core component progressively closer together.

The second component formation may be a superior component front formation comprised in the superior component. The superior component front formation may be towards an edge of the superior component at which the core component is first received upon insertion of the core component. The second core formation may be a superior core front formation comprised in the core component. The superior core front formation may be towards an edge of the core component opposite the edge first received between the inferior and superior components during insertion of the core component. The superior component front formation and the superior core front formation may inter-engage when the core component is fully inserted to present a barrier to separation of the core component and superior component in the separation direction. The superior component front formation and the superior core front formation may inter-engage and the superior component rear formation and the superior core rear formation may also inter-engage to present barriers to separation at opposite edges of the core component. The superior component front formation and the superior core front formation, and the superior component rear formation and the superior core rear formation may be operative to stop the superior component lifting or at least limit an extent to which the superior component can lift from the core component.

The superior component front formation may comprise a recess and the superior core rear formation may comprise a protrusion, the protrusion received on the recess when the core component is fully inserted. Furthermore, the superior component front formation and the superior core front formation may be shaped to draw the superior component and the core component progressively closer together during a last stage of insertion of the core component. Each of the superior component front formation and the superior core front formation may define an inclined surface, the two inclined surfaces sliding over each other to draw the superior component and the core component progressively closer together. The superior component front formation and the superior core front formation may start to inter-engage with each other at a same extent of insertion of the core component as when the superior component rear formation and the superior core rear formation start to inter-engage with each other. Opposite edges of the core component are thus drawn towards the superior component simultaneously as the core component is inserted.

References herein to anterior or to anterior aspect may be to the anterior aspect of the intervertebral fusion device itself and not to the anterior aspect of the patient. The anterior aspect of the intervertebral fusion device itself may therefore mean the aspect at which the core component is inserted between the superior and inferior components. Correspondingly, references herein to posterior or to posterior aspect may be to the posterior aspect of the intervertebral fusion device itself and not to the posterior aspect of the patient. The anterior and posterior aspects are oppositely directed. The intervertebral fusion device may be an anterior, anterior oblique, lateral or direct lateral intervertebral fusion device.

The superior component, the inferior component and the core component may be separate components. Furthermore, the superior component and the inferior component may be disconnected from each other in the absence of the core component. Having separate inferior and superior components and core component and more specifically disconnected inferior and superior components means that the components may be introduced to the intervertebral space more gently compared with known single piece intervertebral fusion devices which often need to be hammered into place. Such a less gentle insertion process may damage the intervertebral fusion device, may increase time required for the intervertebral fusion device to settle in the intervertebral space, and may result in trauma to vertebral bodies, adjacent soft tissues including neural structures. On the subject of trauma, a device that is hammered into place is liable to create microfractures in the vertebrae which could lead to subsidence of the device into the host bone. Furthermore, having separate components and in particular a core component separate to the inferior and superior components allows for differences in dimensions of intervertebral spaces, differences in angle between the adjacent vertebrae that define the intervertebral space, and degree of spinal alignment and/or correction.

When assembled, the intervertebral fusion device may have a range of length by width from 20 mm by 15 mm to 65 mm by 50 mm. Where there is an oblique intervertebral fusion device, the range of length by width may be from 20 mm by 15 mm to 40 mm by 35 mm. Where there is an anterior intervertebral fusion device, the range of length by width may be from 20 mm by 20 mm to 50 mm by 50 mm. Where there is a lateral intervertebral fusion device, the range of length by width may be from 40 mm by 18 mm to 65 mm by 40 mm. A height of the intervertebral fusion device may be 5 mm to 15 mm at the posterior aspect.

According to a fourth further aspect of the present invention there is provided a method of installing an intervertebral fusion device in an intervertebral space between first and second adjacent vertebrae, the intervertebral fusion device comprising a superior component having a superior component top side and a superior component bottom side, an inferior component having an inferior component top side and an inferior component bottom side, and a core component, the method comprising:

positioning the superior component and the inferior component relative to each other such that the superior component bottom side and the inferior component top side oppose each other;

inserting the core component between the superior and inferior components whereby a separation between the superior and inferior components is determined; and disposing the intervertebral fusion device in the intervertebral space such that the superior component top side abuts against the first vertebra and the inferior component bottom side abuts against the second vertebra, wherein the core component comprises a first core formation and one of the inferior component top side and the superior component bottom side comprises a first component formation, the first core formation inter-engaging with the first component formation to present a barrier to separation of the core component and the corresponding one of the inferior and superior components from each other during insertion of the core component, wherein the core component comprises a core profile and the other of the inferior component top side and the superior component bottom side comprises a component profile, the core profile and the component profile cooperating with each other during insertion of the core component to thereby guide the core component, there being no barrier to separation of the core component and the corresponding one of the inferior and superior components from each other during insertion of the core component, and wherein the core component comprises a second core formation and the other of inferior component top side and the superior component bottom side comprises a second component formation, the second core formation inter-engaging with the second component formation to present a barrier to separation of the core component and the corresponding one of the inferior and superior components from each other when the core component is fully received between the inferior and superior components.

The intervertebral fusion device may be installed in an intervertebral space by positioning the superior component and the inferior component relative to each other in the intervertebral space before the core component is inserted between the superior and inferior components. Alternatively, the intervertebral fusion device may be installed in an intervertebral space by positioning the superior component and the inferior component relative to each other at a location apart from the intervertebral space and inserting the core component between the superior and inferior components at this location before the thus assembled intervertebral fusion device is installed in the intervertebral space.

Further embodiments of the fourth further aspect of the present invention may comprise one or more features of the third further aspect of the present invention.

BRIEF DESCRIPTION OF DRAWINGS

Further features and advantages of the present invention will become apparent from the following specific description, which is given by way of example only and with reference to the accompanying drawings, in which.

DESCRIPTION OF EMBODIMENTS

Figure 2A:
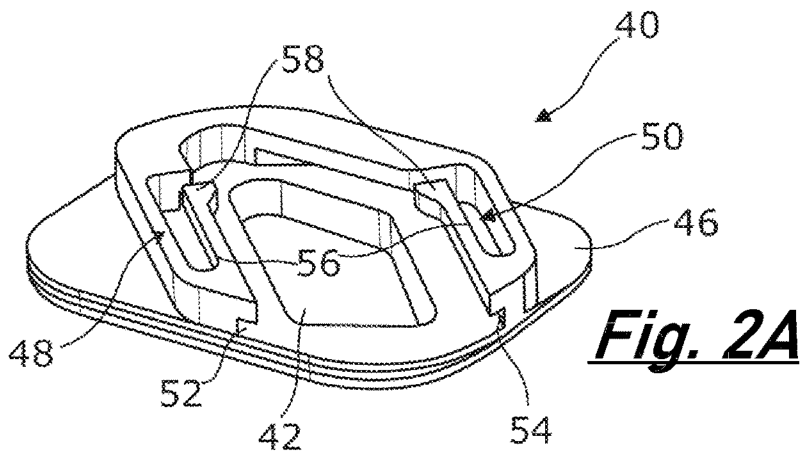
FIG. 2A is a perspective view of an inferior component of the intervertebral fusion device according to the first embodiment.
Figure 2B:
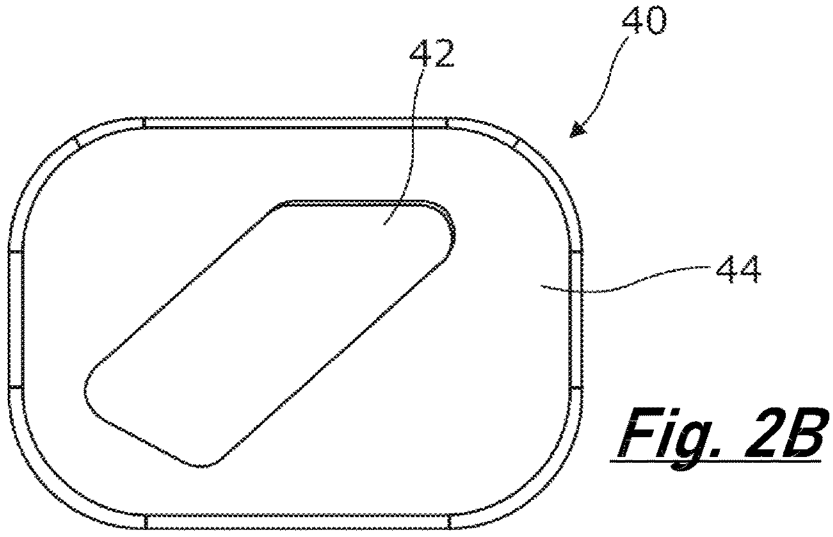
FIG. 2B is a view from above of the inferior component of FIG. 2A.
Figure 2C:
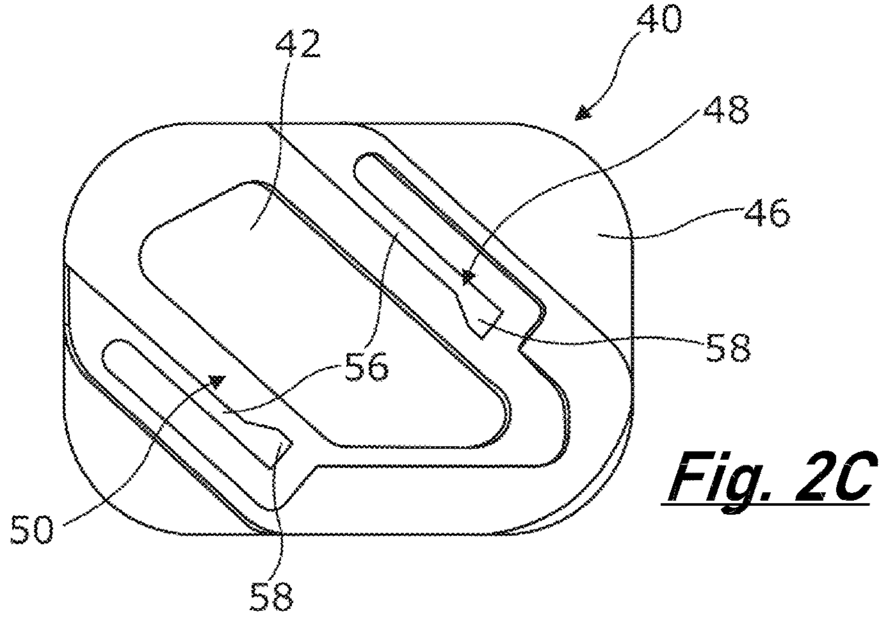
FIG. 2C is a view from below of the inferior component of FIG. 2A.
Figure 3A:
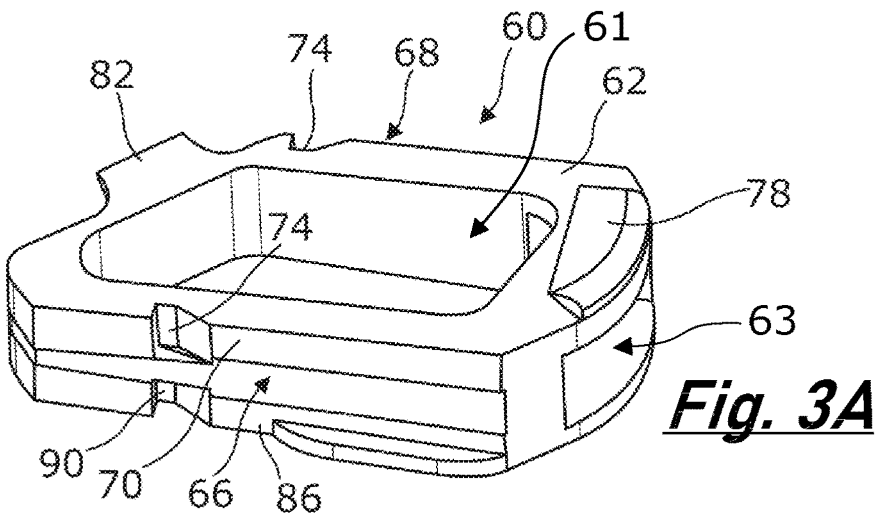
FIG. 3A is a perspective view of a core component of the intervertebral fusion device according to the first embodiment.
Figure 3B:
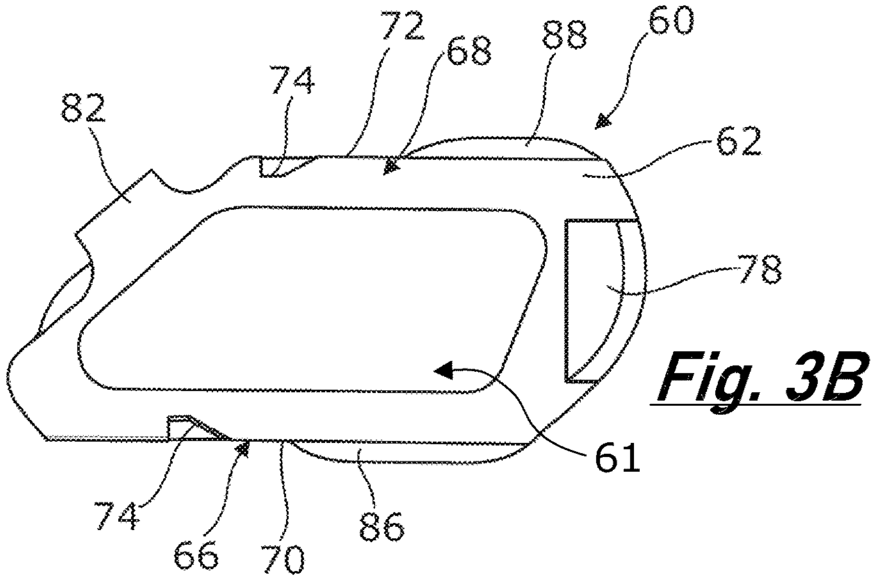
FIG. 3B is a view from above of the core component of FIG. 3A.
Figure 3C:
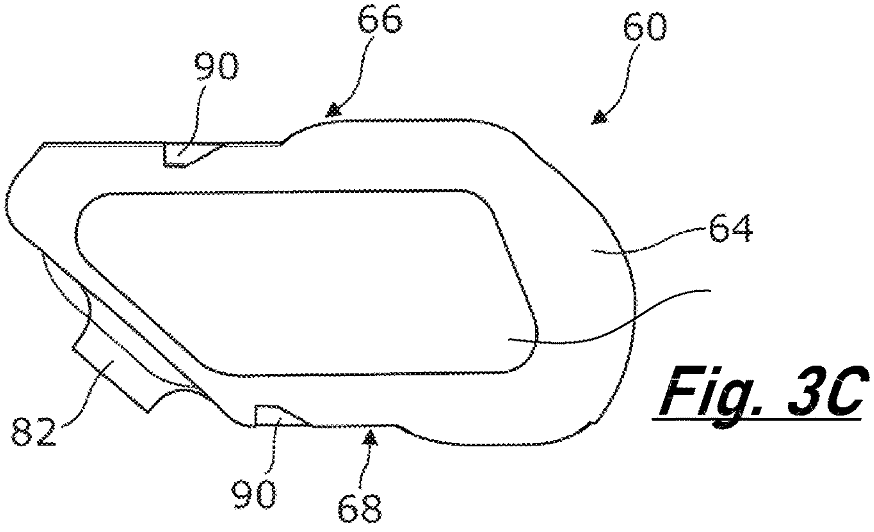
FIG. 3C is a view from below of the core component of FIG. 3A.
Figure 4A:
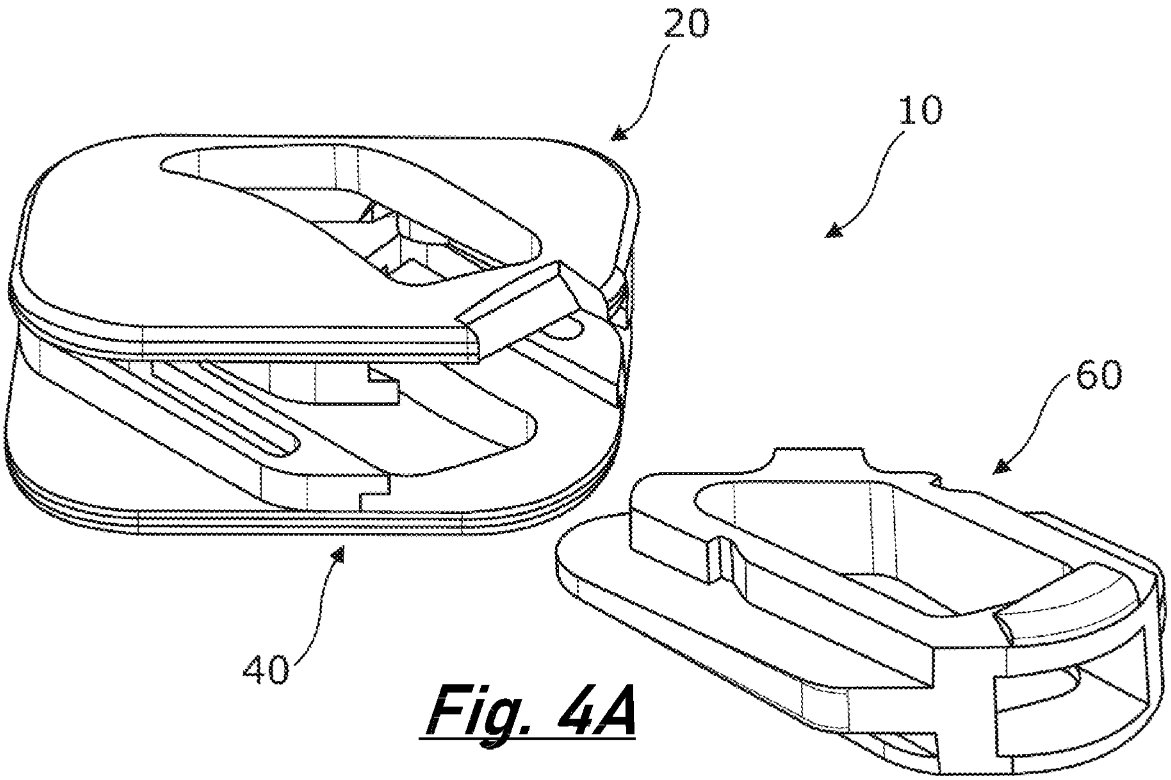
FIG. 4A shows the core component of FIGS. 3A to 3C before insertion between the superior and inferior components of FIGS. 1A to 20.
Figure 4B:
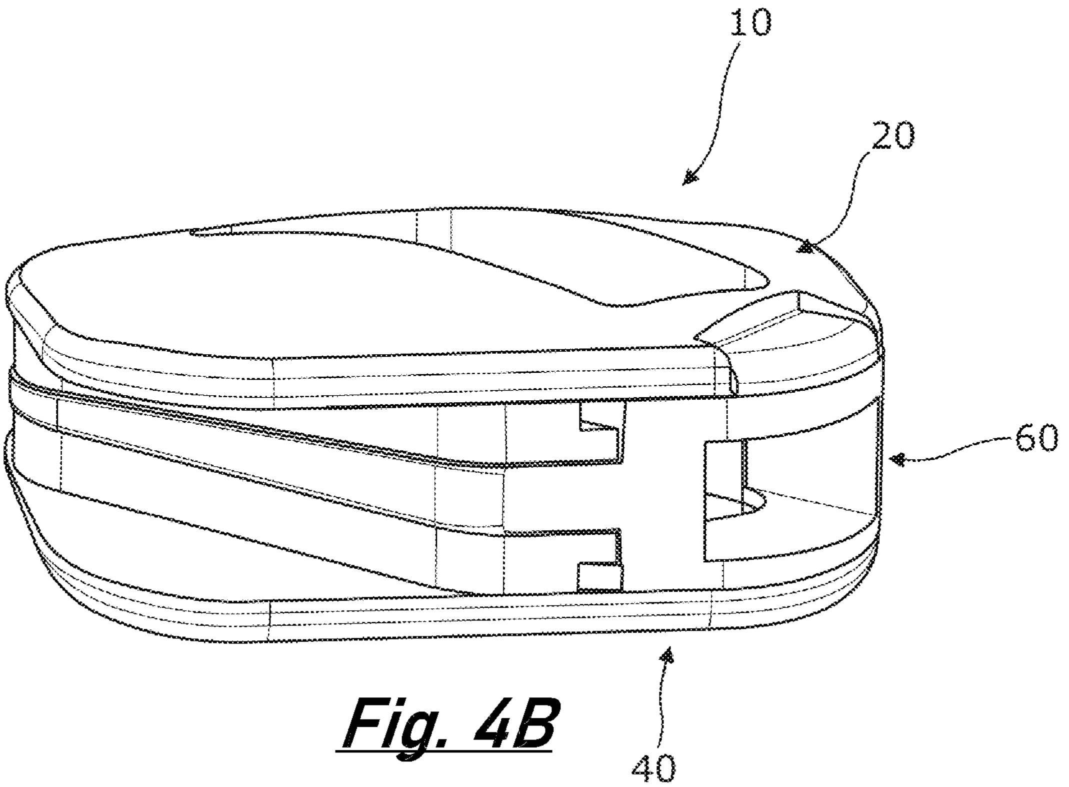
FIG. 4B shows the core component of FIG. 4A after insertion between the superior and inferior components of FIG. 4A.

A superior component, an inferior component and a core component of a first embodiment of intervertebral fusion device 10 are shown respectively in FIGS. 1A to 1C, 2A to 2C and 3A to 3C. The superior component constitutes a superior endplate of the intervertebral fusion device 10 and the inferior component constitutes an inferior endplate of the intervertebral fusion device 10. FIG. 4A shows the core component of FIGS. 3A to 3C before insertion between the superior and inferior components of FIGS. 1A to 2C. FIG. 4B shows the core component of FIG. 4A after insertion between the superior and inferior components of FIG. 4A.

As mentioned above, the intervertebral fusion device 10 of FIGS. 1A to 4B comprises a superior component 20, an inferior component 40 and a core component 60. Each of the superior component 20 and the inferior component 40 is generally of the form of a plate, albeit a plate having structures thereon and a large bone graft aperture 22, 42 therethrough. The superior component 20 has a superior component top side 24 and the inferior component 40 has an inferior component bottom side 44. The core component 60 has the form of a frustum of a wedge. Use of core components of different thicknesses and/or different extents of tapering wedge and with the same superior component 20 and inferior component 40 provides for different heights and angles of intervertebral fusion device 10. When the intervertebral fusion device 10 is being brought into use, the superior component and the inferior component 40 are placed in the intervertebral space and are set at a desired orientation relative to the vertebrae defining the intervertebral space. The core component 60 is manoeuvred past adjacent blood vessels and positioned relative to the superior component 20 and the inferior component 40 as shown in FIG. 4A. Then the core component 60 is positioned between edges of the superior component 20 and the inferior component 40 with the thin radiused edge of the core component foremost, before the core component is progressively inserted between the superior component and the inferior component until fully received between the superior component and the inferior component. FIG. 4B shows the intervertebral fusion device 10 when the core component 60 is fully received between the superior component 20 and the inferior component 40. When the intervertebral fusion device is in the disposition shown in FIG. 4B, the superior component top side 24 abuts against a first vertebra defining the intervertebral space in part and the inferior component bottom side 44 abuts against a second vertebra defining the intervertebral space in part.

Figure 1A:
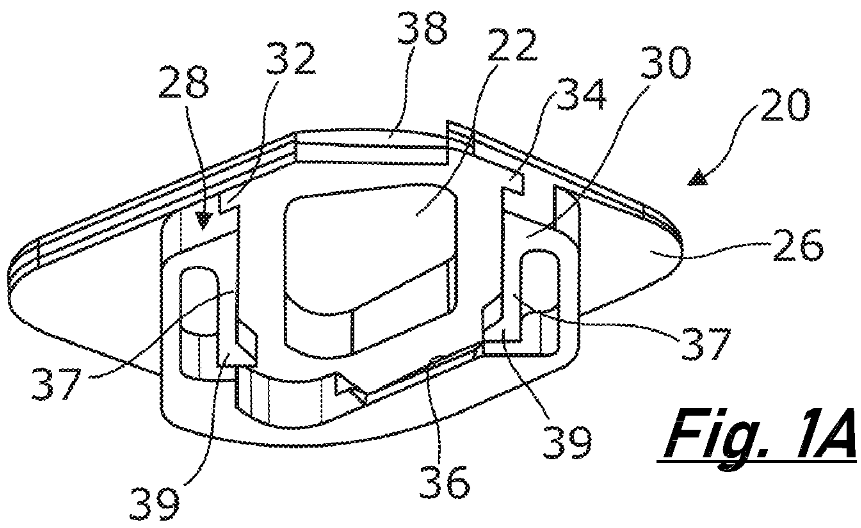
FIG. 1A is a perspective view of a superior component of an intervertebral fusion device according to a first embodiment of the present invention.
Figure 1B:
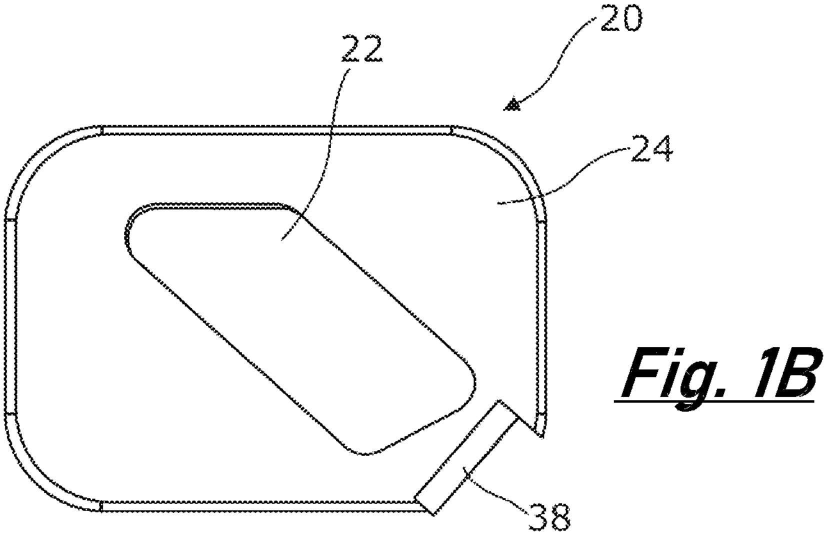
FIG. 1B is a view from above of the superior component of FIG. 1A.
Figure 1C:
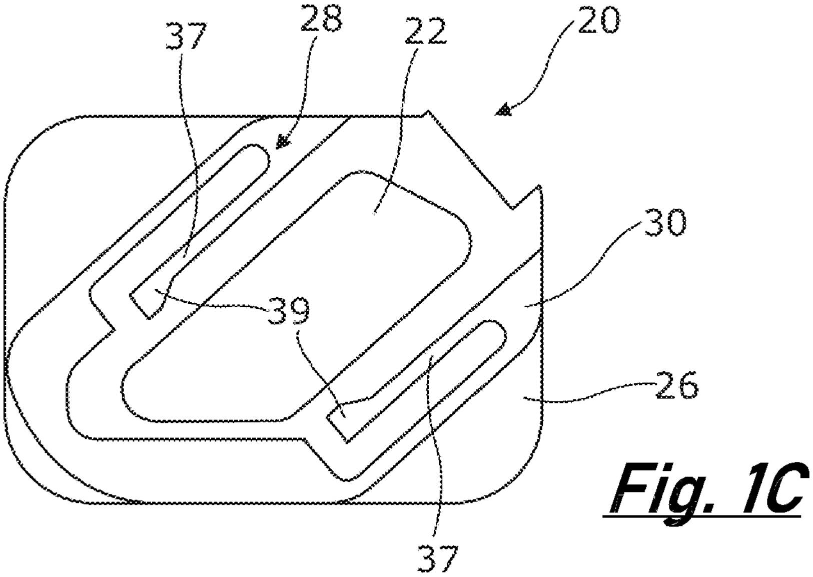
FIG. 1C is a view from below of the superior component of FIG. 1A.

The superior component 20 will now be described further with reference to FIGS. 1A to 1C. The superior component 20 has a superior component top side 24, a superior component bottom side 26, a first lateral side 28 and a second lateral side 30. The first and second lateral sides 28, 30 are spaced apart from respective corners of the superior component top side 24 whereby the superior component bottom side 26 is planar between a lateral side 28, 30 and a corner. The superior component 20 comprises a first superior component formation 32 and a second superior component formation 34. The first superior component formation 32 is on the first lateral side 28 and the second superior component formation 34 is on the second lateral side 30. The first superior component formation 32 and the first superior core formation, the latter of which is described below, abut and the second superior component formation 34 and the second superior core formation, the latter of which is described below, abut whereby there is substantially no movement of the core component 60 relative to the superior component 20 in a direction which is both orthogonal to the direction of insertion of the core component and orthogonal to the direction of separation of the superior and inferior components. Each of the first and second superior component formations 32, 34 defines a groove which extends from the edge of the superior component 20 that first receives the core component 60 when the core component is being inserted. As will become clear from the description of the core component below, the first and second superior core formations abut against their respective first and second superior component formations and such that no parts of the first and second superior core formations are received in the grooves defined by the first and second superior component formations.

Considering the first and second superior component formations 32, 34 further, each formation is constituted by a main body in the form of a finger 37 which extends from a proximal end of the finger at an anterior edge of the superior component across the superior component towards the posterior edge of the superior component. The finger 37 therefore extends in a direction of insertion of the core component. The finger 37 is unsupported and unattached along its length with the exception of its proximal end. The superior component and the finger are formed of a material of sufficient yield strength that the finger functions as a cantilever spring. Although not shown in FIG. 1A or FIG. 1C, the finger 37 is tapered in certain forms to determine stiffness and hence extent of deflection. Furthermore, a radius of the interface between the finger and the part of the superior component from which the finger extends is determined to control stiffness of the finger. The finger 37 defines a protrusion 39 at its distal end with the protrusion extending in a transverse direction of the superior component. The fingers 37 of the first and second superior component formations 32, 34 are mirror images of each other whereby their two protrusions 39 oppose each other and extend towards each other. In view of the cantilever sprung nature of each finger 37, application of a load to the protrusion 39 in a transverse direction towards a respective lateral side deflects the finger to thus store energy in the finger to provide for urging of the protrusion 39 in the opposite direction. As described below, the finger 37 is deflected by a leading edge of the core component 60 bearing against the protrusion 39.

The superior component 20 also has a superior component rear formation 36 which extends along a back edge of the superior component, the back edge opposite the side at which the core component is first received upon insertion. The superior component rear formation 36 comprises an edge from which an inclined surface extends. The superior component 20 also has a superior component front formation 38 at the side at which the core component is first received upon insertion of the core component. The superior component front formation 38 has the form of a recess having an edge from which an inclined surface extends to the superior component top surface 24. As can be seen from FIG. 1B, the superior component top surface 24 is a rectangle with rounded corners.

The inferior component 40 will now be described further with reference to FIGS. 2A to 2C. The inferior component 40 has an inferior component top side 46, an inferior component bottom side 44, a first lateral side 48 and a second lateral side 50. The first and second lateral sides 48, 50 are spaced apart from respective corners of the inferior component bottom side 44 whereby the inferior component top side 46 is planar between a lateral side 48, 50 and a corner. The inferior component comprises a first inferior component formation 52 and a second inferior component formation 54. The first inferior component formation 52 is towards the first lateral side 48 and the second inferior component formation 54 is towards the second lateral side 50. The first and second inferior component formations 52, 54 oppose each other and are spaced apart in a direction orthogonal to the direction of insertion of the core component between the inferior and superior components. The core component 60 is received between the first and second inferior component formations 52, 54 during insertion. Each of the first and second inferior component formations 52, 54 defines a groove which extends from the edge of the inferior component 40 that first receives the core component 60 when the core component is being inserted.

The first and second inferior component formations 52, 54 are constituted in the same fashion as the first and second superior component formations 32, 34 described above. Each of the first and second inferior component formations 52, 54 is therefore constituted by a finger 56 which extends from a proximal end of the finger at an anterior edge of the inferior component 40 across the inferior component towards the posterior edge of the inferior component. The finger 56 therefore extends in a direction of insertion of the core component. The finger 56 is unsupported and unattached along its length with the exception of its proximal end. The finger 56 defines a protrusion 58 at its distal end with the protrusion extending in a transverse direction of the superior component. The fingers 56 of the first and second inferior component formations 52, 54 are mirror images of each other whereby their two protrusions 58 oppose each other and extend towards each other. In view of the cantilever sprung nature of each finger 58, application of a load to the protrusion 58 in a transverse direction towards a respective lateral side deflects the finger to thus store energy in the finger to provide for urging of the protrusion 58 in the opposite direction. As described below, the finger 58 is deflected by a leading edge of the core component 60 bearing against the protrusion 58. As can be seen from FIG. 2B, the inferior component bottom surface 44 is a rectangle with rounded corners.

The core component 60 will now be described further with reference to FIGS. 3A to 3C. As will become apparent from the following description, the core component of FIGS. 3A to 3C differs from the core component of FIGS. 4A and 4B. Nevertheless, the core component of FIGS. 3A to 3C functions and engages with the superior and inferior components in the same way as the core component of FIGS. 4A and 4B. However, the core component of FIGS. 3A to 3C is narrower than the core component of FIGS. 4A and 4B which provides for greater ease of insertion of the core component of FIGS. 3A to 3C.

The core component 60 has a core component top side 62 and a core component bottom side 64. The core component top side 62 faces the superior component bottom side 26 and the core component bottom side 64 faces the inferior component top side 46 when the core component is received between the superior and inferior components 20, 40 as shown in FIG. 4B. As can be seen from FIGS. 3B and 3C, the depth of the core component is greater than its width. Each of the core component top side 62 and the core component bottom side 64 extends over an area that is 25% smaller than an area of each of the superior component bottom side 26 and the inferior component top side 46. Having a core component of such shape and of smaller extent than each of the superior and inferior components provides for ease of in-situ insertion of the core component between the superior and inferior components.

The core component 60 has first 66 and second 68 lateral sides which face in opposite directions and which each face in a direction orthogonal to a direction of insertion of the core component and to a direction of separation of the inferior and superior components during insertion. A first superior core formation 70 is on the first lateral side 66 and a second superior core formation 72 is on the second lateral side 68. Each of the first and second superior core formations 70, 72 comprises a planar surface that extends from near the rounded leading end of the core component to a recess 74 and a further planar surface that extends away from the recess to near a trailing end of the core component. As can be seen from FIGS. 4A and 4B, when the core component is inserted between the superior and inferior components, the first and second superior component formations 32, 34 and the first and second superior core formations 70, 72 are located on their respective superior component and core component such that the first superior component formation and the first superior core formation abut and the second superior component formation and the second superior core formation abut whilst allowing the core component to be slid progressively further between the superior and inferior components. The formations therefore cooperate to define a linear track along which the core component travels. When the core component is fully received between the superior and inferior components, each protrusion 39 on an end of a finger 37 of the superior component is received under spring bias in its respective recess 74 in the core component to thereby present resistance to expulsion of the core component from between the superior and inferior components.

The core component 60 also has an anterior formation 78 on its upper side 62 in the form of a protrusion at the anterior edge of the core component. The anterior formation 78 has a side oriented towards the posterior edge of the core component which slopes away from a distal surface of the anterior formation towards the anterior edge. As described above, the superior component 20 has a superior component front formation 38. When the core component is nearly fully inserted between the inferior and superior components, the inclined surface of the superior component front formation 38 rides over the sloping side of the anterior formation 78 to draw the superior component down onto the core component.

The core component 60 also has a posterior protrusion 82 which slopes away from a distal edge of the posterior protrusion 82 lying in the plane of the core component top side 62. As described above, the superior component 20 has a superior component rear formation 36 which extends along a back edge of the superior component. When the core component is nearly fully inserted between the inferior and superior components, the sloping surface of the posterior protrusion 82 rides over the inclined surface of the superior component rear formation 36 to draw the superior component down onto the core component.

The core component further comprises a first inferior core formation 86 on the first lateral side 66 of the core component and a second inferior core formation 88 on the second lateral side 68 of the core component. Each of the first and second inferior core formations 86, 88 comprises a planar surface that extends from near the rounded leading end of the core component to a recess 90, and a further planar surface that extends away from the recess to an elongate protrusion which extends to near a trailing end of the core component. The elongate protrusions are shaped to be received in a respective one of the grooves defined by the first and second inferior component formations 52, 54. As can be seen from FIGS. 4A and 4B, when the core component is inserted between the superior and inferior components, the first and second inferior core formations 86, 88 and the first and second inferior component formations 52, 54 are located on their respective inferior component and core component such that the first inferior component formation and the first inferior core formation abut, with elongate protrusion slidably received in recess, and the second inferior component formation and the second inferior core formation abut, with elongate protrusion slidably received in recess. The formations therefore cooperate to define a linear track along which the core component travels while resisting separation of the core component and inferior component and restraining relative movement of the core component and inferior component in the transverse direction. When the core component is fully received between the superior and inferior components, each protrusion 58 on an end of a finger 56 of the inferior component is received under spring bias in its respective recess 90 in the core component to thereby present resistance to expulsion of the core component from between the superior and inferior components.

The core component 60 further defines a bone graft material holding space 61 having a holding space opening in each of the core component top side 62 and the core component bottom side 64. The bone graft material holding space 61 is defined by walls on four sides of the bone graft material holding space. The side of the bone graft material holding space 61 at the anterior end of the core component 60 is open in part to define a bone graft port 63 whereby bone graft material is injected into the bone graft material holding space when the intervertebral fusion device is in the intervertebral space. Injected bone graft material moves from the bone graft material holding space 61, such as when under pressure, and through the bone graft apertures 22, 42 in the superior and inferior components 20, 40.

As can be seen from a comparison of FIG. 3A with FIG. 4A, the core component of FIG. 3A lacks the elongate protrusion of the core component of FIG. 4A that extends between the leading and trailing ends of the core component and is situated between the superior and inferior core formations on each of the first and second lateral sides. The absence of these elongate protrusions from the core component of FIG. 3A provides a narrower core component which is even more readily inserted than the core component of FIG. 4A.

Figure 5:
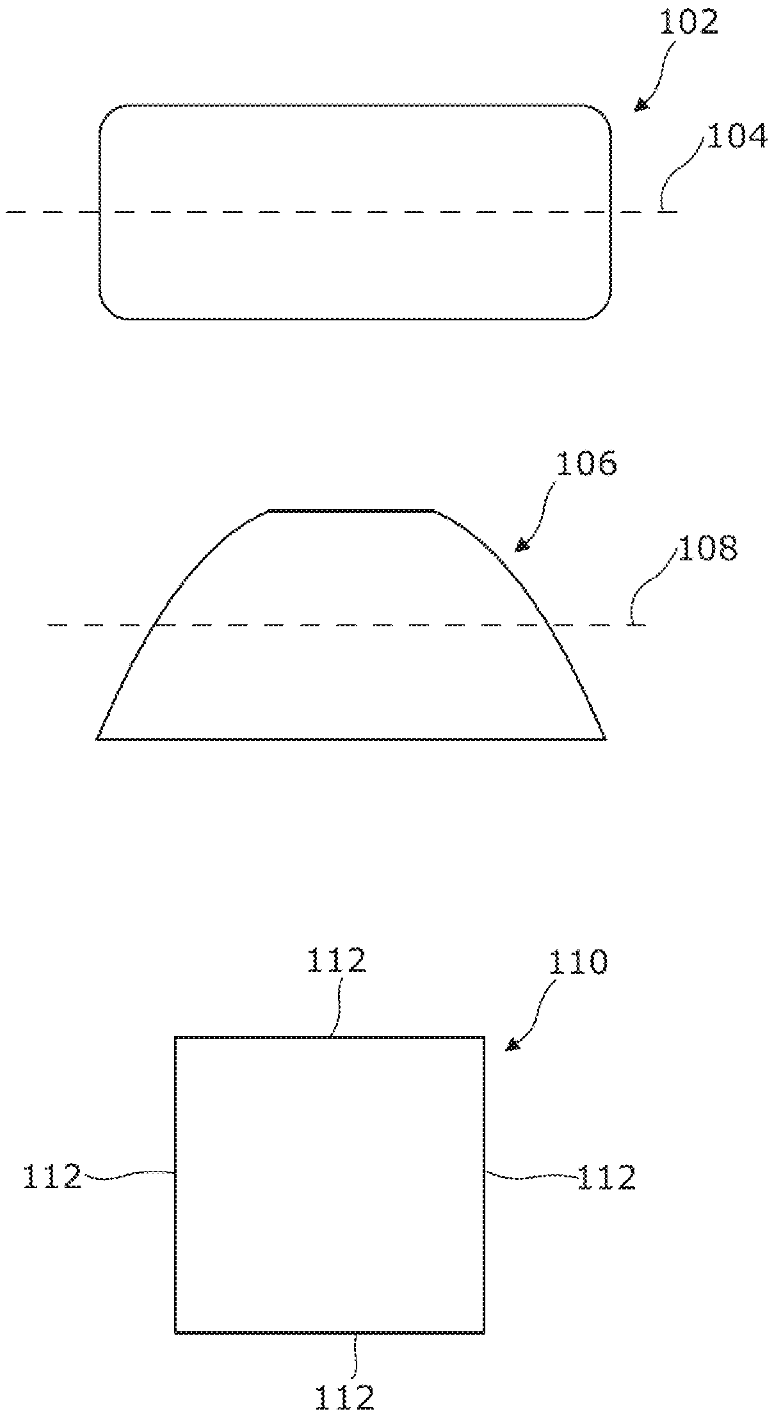
FIG. 5 shows different shapes of superior component top side and inferior component bottom side.

Different shapes of superior component top side and inferior component bottom side are shown in FIG. 5. The first shape 102 is an oblong rectangle with rounded corners. The major axis 104 (i.e. a line that passes through the center of each short side of the superior component top side/inferior component bottom side) is indicated with a dashed line. The second shape 106 is an oblong rectangle in which each of two corners at opposite ends of a long edge of the rectangle is rounded with the other two corners not being rounded. Each of the superior component top side and the inferior component bottom side may therefore have the shape shown in FIG. 5 or be more ‘D’ shaped. The major axis 108 is indicated with a dashed line. The direction of insertion of the core component 60 between the superior and inferior components 20, 40, as described above, is oblique to the major axis. The third shape 110 is a square in which the four edges 112 are of the same length. The direction of insertion of the core component 60 between the superior and inferior component 20, 40, as described above, is oblique to each of the four edges 112.

Figure 6A:
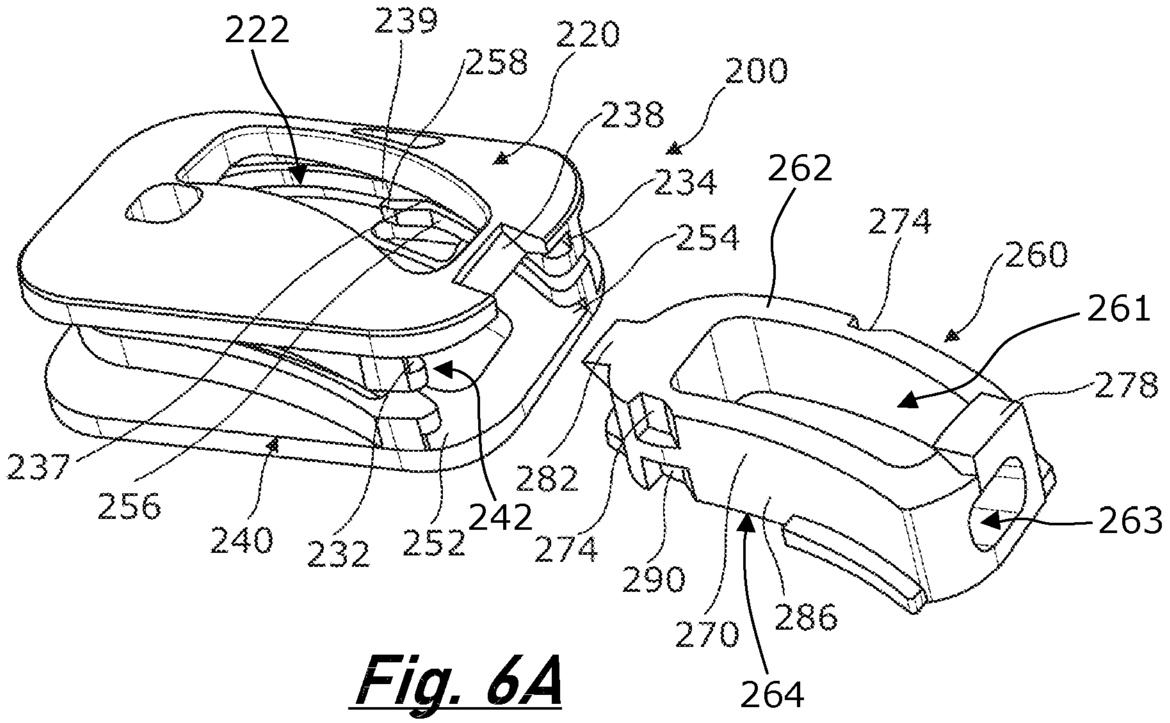
FIG. 6A shows a core component before insertion between superior and inferior components according to a second embodiment.

A superior component, an inferior component and a core component of a second embodiment of intervertebral fusion device 200 are shown in FIG. 6A before insertion of the core component between the superior and inferior components.

Figure 6B:
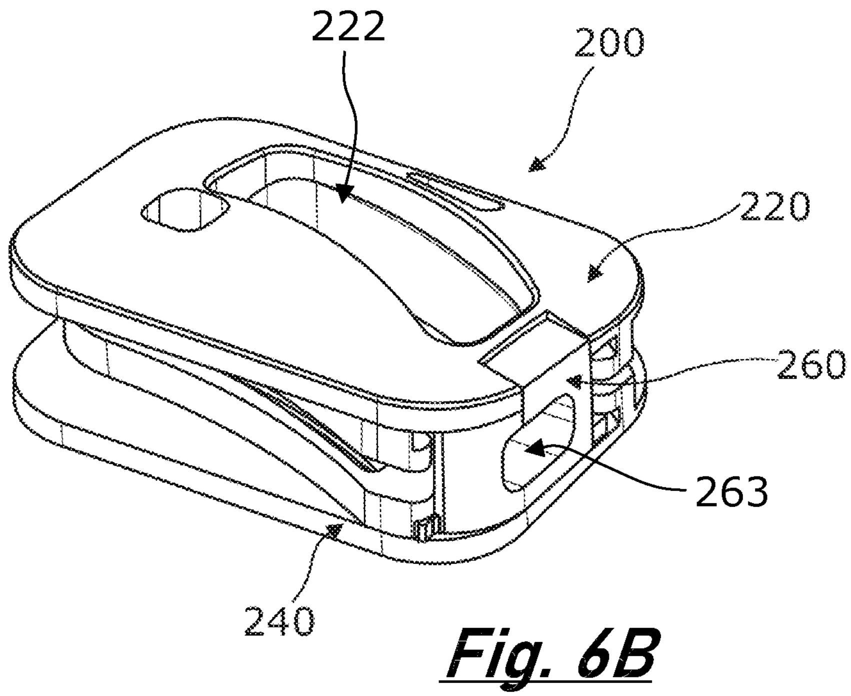
FIG. 6B shows the core component of FIG. 6A after insertion between the superior and inferior components of FIG. 6A.

The superior component constitutes a superior endplate of the intervertebral fusion device 200 and the inferior component constitutes an inferior endplate of the intervertebral fusion device 200. FIG. 6B shows the core component of FIG. 6A after insertion between the superior and inferior components of FIG. 6A.

As can be seen from FIG. 6A, the superior component top side and inferior component bottom side are of the same shape as the first embodiment. For example, each of the superior component 220 and the inferior component 240 is generally of the form of a plate, albeit a plate having structures thereon and a large bone graft aperture 222, 242 therethrough. Furthermore, the superior component 220, the inferior component 240 and the core component 260 comprise the same features as the first embodiment. For example, the first and second superior component formations 232, 234 in the second embodiment are each constituted by a main body in the form of a sprung finger 237 with the finger having a protrusion 239 at its end. The first and second inferior component formations 252, 254 in the second embodiment are each constituted by a finger 256 with the finger having a protrusion 258 at its end. By way of further example, the superior component of the second embodiment has a superior component front formation 238 in the form of a recess which cooperates with an anterior formation 278 on the core component to draw the superior component and core component together. The core component of the second embodiment also has a posterior protrusion 282 which cooperates with a superior component rear formation to draw the superior component and core component together.

By way of yet further example, each of the first 270 and second superior core formations of the second embodiment comprises a planar surface that extends from near the leading end of the core component to a recess 274 and a further planar surface that extends away from the recess to near a trailing end of the core component. Each of the first 286 and second inferior core formations of the second embodiment comprises a planar surface that extends from near the leading end of the core component to a recess 290, and a further planar surface that extends away from the recess to an elongate protrusion which extends to near a trailing end of the core component. The form of the second embodiment is such that the core component engages with the superior and inferior components as described above with reference to the first embodiment.

Furthermore, the core component 260 defines a bone graft material holding space 261 having a holding space opening in each of the core component top side 262 and the core component bottom side 264. The bone graft material holding space 261 is defined by walls on four sides of the bone graft material holding space. The side of the bone graft material holding space 261 at the anterior end of the core component 260 is open in part to define a bone graft port 263 whereby bone graft material is injected into the bone graft material holding space when the intervertebral fusion device 200 is in the intervertebral space. Injected bone graft material moves from the bone graft material holding space 261, such as when under pressure, and through the bone graft apertures 222, 242 in the superior and inferior components 220, 240.

The key difference between the first and second embodiments is the core component following a curved path during insertion of the core component between the superior and inferior components in the second embodiment. The curved path is provided by the first and second superior and inferior component formations 232, 234, 252, 254 being curved with the first and second superior and inferior core formations having corresponding curvatures. The first and second superior and inferior component formations 232, 234, 252, 254 therefore cooperate with their respective first and second superior and inferior core formations by abutting as described with reference to the first embodiment to constrain the core component to follow a curvilinear path during insertion of the core component between the superior and inferior components.

Figure 7A:
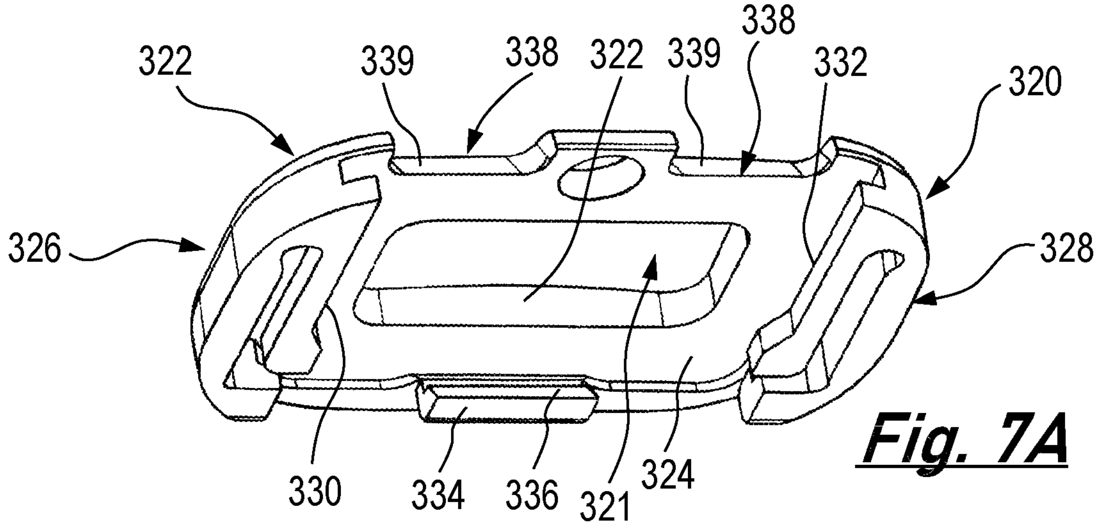
FIG. 7A shows a superior component of a third embodiment of the present invention.
Figure 7B:
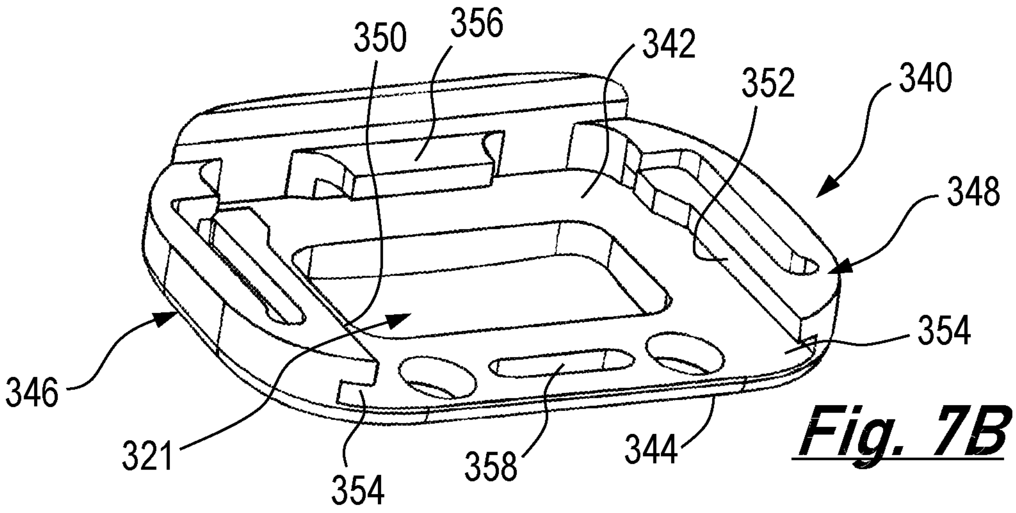
FIG. 7B shows an inferior component of the third embodiment of the present invention.
Figure 7C:
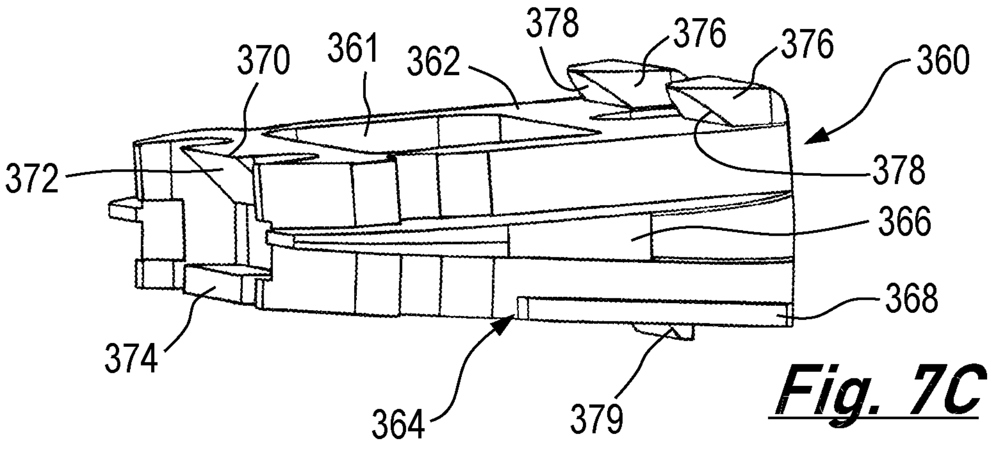
FIG. 7C shows core component of the third embodiment of the present invention.
Figure 8A:
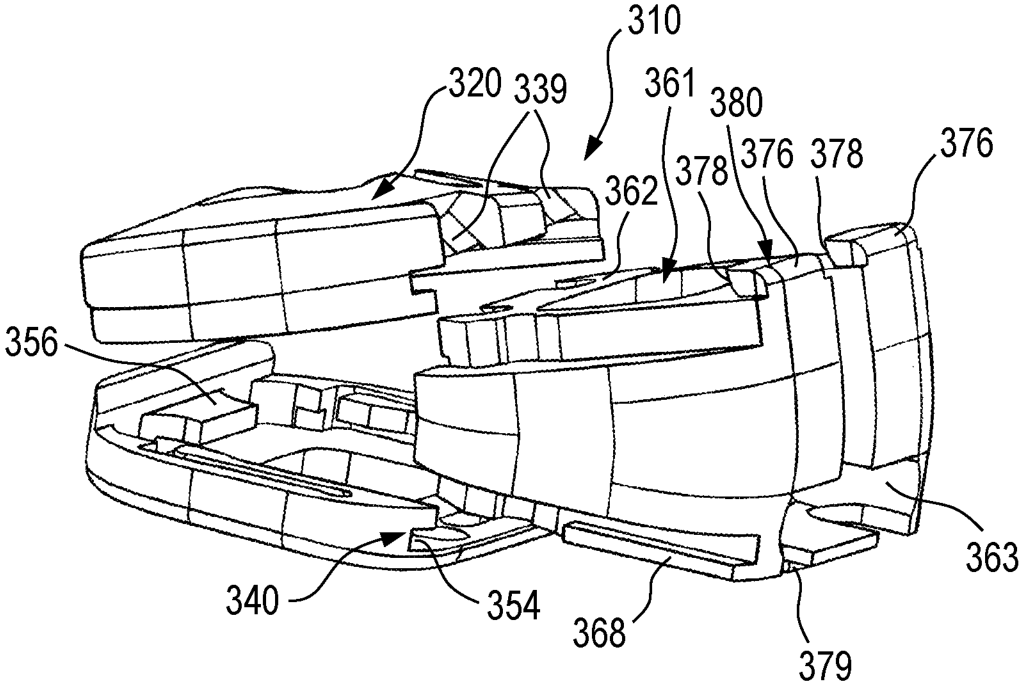
FIG. 8A shows the core component before insertion between the superior and inferior components according to a fourth embodiment.
Figure 8B:
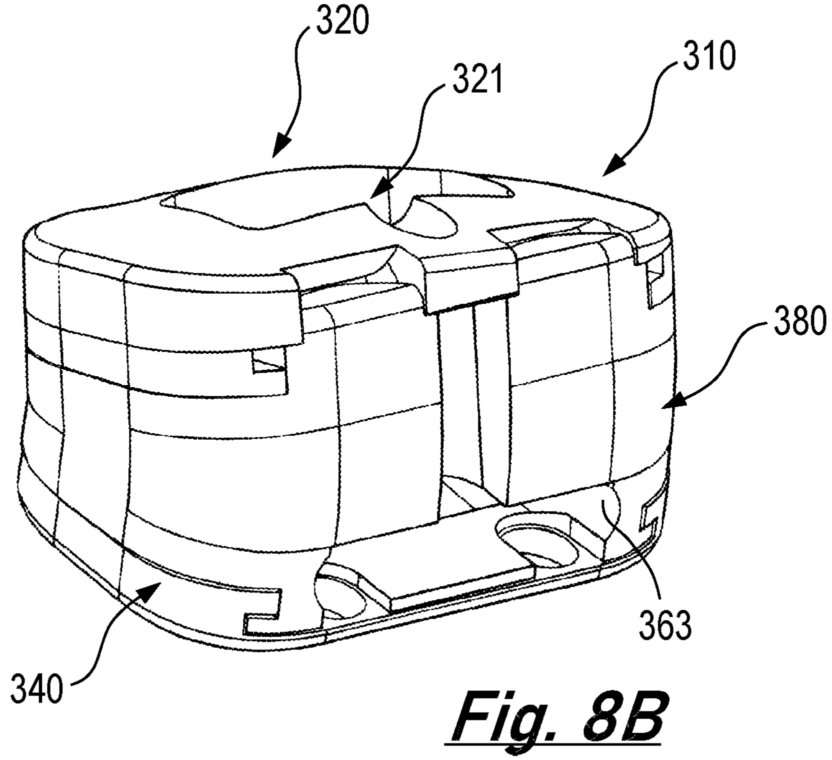
FIG. 8B shows the core component after insertion between the superior and inferior components according to the fourth embodiment.
Figure 9A:
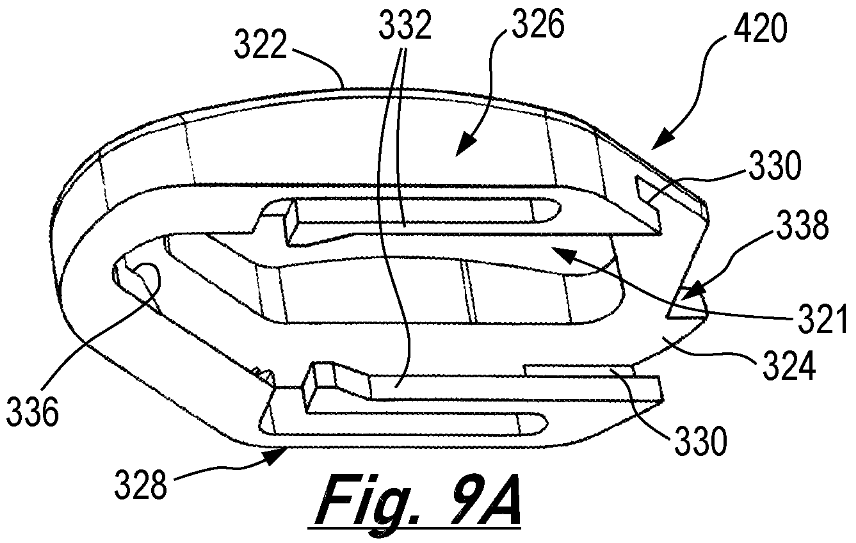
FIG. 9A shows a superior component of a fifth embodiment of the present invention.
Figure 9B:
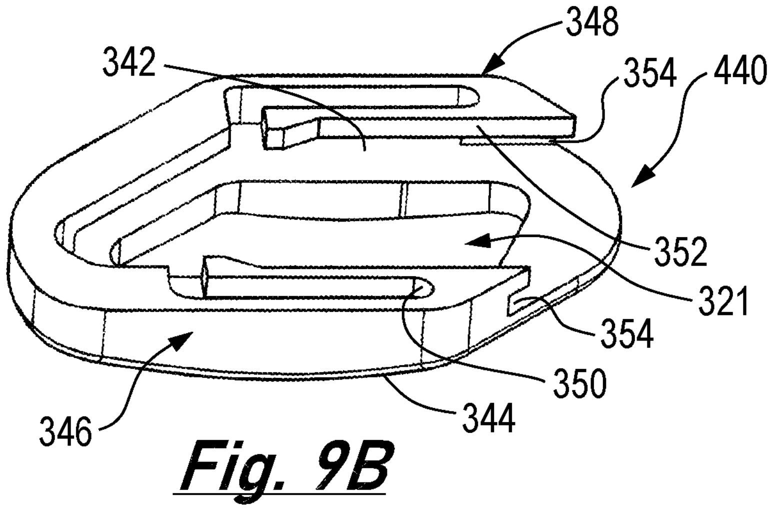
FIG. 9B shows an inferior component of the fifth embodiment of the present invention.
Figure 9C:
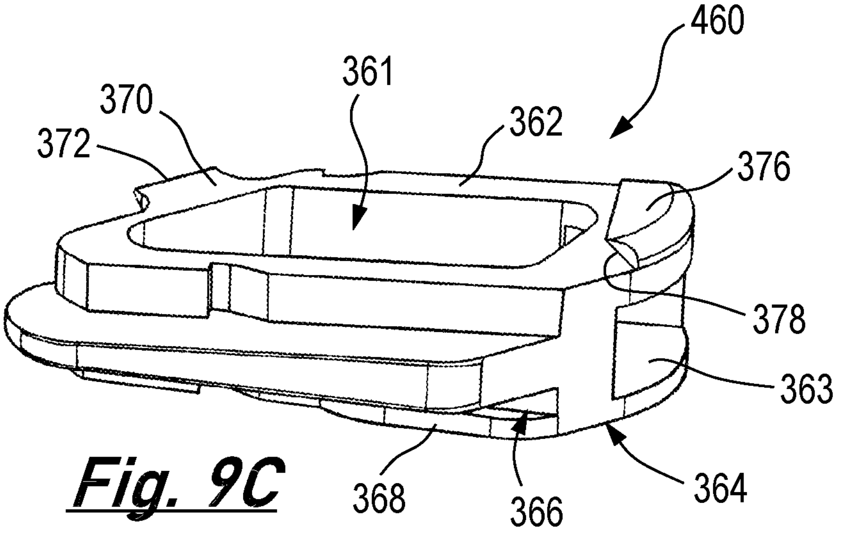
FIG. 9C shows core component of the fifth embodiment of the present invention.

A superior component, an inferior component and a core component of a third embodiment of intervertebral fusion device 310 are shown respectively in FIGS. 7A, 7B and 7C. The superior component constitutes a superior endplate of the intervertebral fusion device 310 and the inferior component constitutes an inferior endplate of the intervertebral fusion device 310. The intervertebral fusion device 310 is an anterior lumbar interbody fusion (ALIF) device. FIG. 8A shows a core component before insertion between the superior and inferior components of FIGS. 7A and 7B according to a fourth embodiment of intervertebral fusion device with the fourth embodiment differing from the third embodiment in respect of the greater height of the core component of the fourth embodiment. FIG. 8B shows the core component of FIG. 8A after insertion between the superior and inferior components.

As mentioned above, the intervertebral fusion device 310 of FIGS. 7A to 8B comprises a superior component 320, an inferior component 340 and a core component 360, 380. Each of the superior component 320 and the inferior component 340 is generally of the form of a plate, albeit a plate having structures thereon and a large bone graft aperture 321 therethrough. The core component 360, 380 has the form of a frustum of a wedge. As can be seen from comparison of FIG. 7C with FIGS. 8A and 8B, the core component of FIG. 7C is thinner than the core component of FIGS. 8A and 8B. What is shown in FIGS. 8A and 8B therefore constitutes a fourth embodiment. Use of core components of different thicknesses and/or different extents of tapering wedge and with the same superior component 320 and inferior component 340 provides for different heights and angles of intervertebral fusion device 310. When the intervertebral fusion device 310 is brought into use, the superior component 320 and the inferior component 340 are placed in the intervertebral space. The core component 360, 380 is positioned relative to the superior component 320 and the inferior component 340 as shown in FIG. 8A. Then the core component 360, 380 is positioned between edges of the superior component 320 and the inferior component 340 with the thin edge of the core component foremost before the core component is progressively inserted between the superior component and the inferior component until fully received between the superior component and the inferior component. FIG. 8B shows the intervertebral fusion device 310 when the core component 360, 380 is fully received between the superior component 320 and the inferior component 340. When in the disposition shown in FIG. 8B, the superior component top side abuts against a first vertebra defining the intervertebral space in part and the inferior component bottom side abuts against a second vertebra defining the intervertebral space in part.

The superior component 320 will now be described further with reference to FIG. 7A. The superior component 320 has a superior component top side 322, a superior component bottom side 324, a first lateral side 326 and a second lateral side 328. The superior component 320 comprise a first superior component profile 330 and a second superior component profile 332. The first superior component profile 330 is on the first lateral side 326 and the second superior component profile 332 is on the second lateral side 328. The first superior component profile and the first superior core profile, which is described below, abut and the second superior component profile and the second superior core profile, which is described below, abut whereby there is substantially no movement of the core component 360, 380 relative to the superior component 320 in a direction transverse to the direction of insertion of the core component between the superior and inferior components.

The superior component 320 also has a superior component rear formation 334 which extends along a back edge of the superior component in a direction transverse to the direction of insertion of the core component, the back edge opposite the edge at which the core component is first received upon insertion. The superior component rear formation 334 comprises a protrusion which defines an inclined surface 336. The superior component 320 also has a superior component front formation at an edge at which the core component is first received upon insertion of the core component. The superior component front formation comprises two recesses 338 which are spaced apart in the transverse direction. A surface of each recess 338 facing opposite the direction of insertion of the core component defines an inclined surface 339. The inclined surfaces 339 can be seen more clearly in FIG. 8A.

The inferior component 340 will now be described further with reference to FIG. 8B. The inferior component 340 has an inferior component top side 342, an inferior component bottom side 344, a first lateral side 346 and a second lateral side 348. The inferior component comprises a first inferior component formation 350 and a second inferior component formation 352. The first inferior component formation 350 is towards the first lateral side 346 and the second inferior component formation 352 is towards the second lateral side 348. The first and second inferior component formations 350, 352 oppose each other and are spaced apart in a direction transverse to the direction of insertion of the core component between the inferior and superior components. The core component 360, 380 is received between the first and second inferior component formations 350, 352 during insertion. Each of the first and second inferior component formations 350, 352 defines a groove 354 which extends from the edge of the inferior component 340 that first receives the core component 360, 380 when the core component is inserted. The opening to the groove 354 faces in the transverse direction.

The inferior component 340 also comprises an inferior component rear formation 356 which extends along a back edge of the inferior component in a direction transverse to the direction of insertion of the core component, the back edge opposite the edge at which the core component is first received upon insertion. The inferior component rear formation 356 defines an elongate protrusion which is spaced apart from the inferior component top side 342 and which extends in the opposite direction to the direction of insertion of the core component 360, 380. The inferior component 340 defines an elongate aperture 358 near the edge of the inferior component that first receives the core component 360, 380 during insertion. The elongate aperture 358 extends in the transverse direction and is located centrally between the first and second inferior component formations 350, 352.

The core component 360 will now be described further with reference to FIG. 7C. As described above, the core component 360 has the form of a frustum of a wedge. The core component 360 has an upper side 362 and a lower side 364, the core component 360 configured to be inserted between the superior and inferior components 320, 340 such that the upper side 362 faces the superior component bottom side 324 and the lower side 364 faces the inferior component top side 342. The core component 360 has a first lateral side 366 and a second lateral side (not seen in FIG. &C) which each face in a direction orthogonal to a direction of insertion of the core component and to a direction of separation of the inferior and superior components, with the first and second lateral sides facing in opposite directions. A first inferior core formation 368 is on the first lateral side 366 and a second inferior core formation (not seen in FIG. 7C) is on the second lateral side. The first and second inferior core formations are of the same albeit mirror image form as each other. Each of the first and second inferior core formations 368 defines an elongate protrusion which extends in the transverse direction and from about half way along the core component 360 from the edge of the core component first received between the inferior and superior components to the opposite edge of the core component.

The core component 360 also comprises a superior core rear formation 370 which extends adjacent the upper side 362 and along an edge of the core component which is first received between the inferior and superior components during insertion of the core component. The superior component rear formation 370 comprises a protrusion which defines an inclined surface 372 which faces obliquely away from the core component and down from the upper side 362. The core component 360 further comprises an inferior core rear formation 374 in the form of a protrusion which extends from the lower side 364 and along the edge of the core component which is first received between the inferior and superior components during insertion of the core component.

The core component 360 also comprises a superior core front formation towards an edge opposite the edge first received between the inferior and superior components during insertion of the core component. The superior core front formation comprises two protrusions 376. The two protrusions 376 extend up from the upper side 362 and are spaced apart from each other in the transverse direction. Each of the protrusions 376 defines an inclined surface 378 which faces obliquely down towards the upper side 362 and towards the edge first received between the inferior and superior components during insertion. The core component 360 further comprises in its lower side 364 a living hinge which defines a protrusion 379 thereon. Inherent spring bias of the living hinge urges the protrusion 379 towards the inferior component 340 when the core component 360 is received between the superior and inferior components 320, 340.

Furthermore, the core component 360, 380 defines a bone graft material holding space 361 having a holding space opening in each of the core component upper side 362 and lower side 364. The bone graft material holding space 361 is defined by walls on four sides of the bone graft material holding space. The side of the bone graft material holding space 361 at the anterior end of the core component 360, 380 is open in part to define a bone graft port 363 whereby bone graft material is injected into the bone graft material holding space when the intervertebral fusion device 310 is in the intervertebral space. Injected bone graft material moves from the bone graft material holding space 361, such as when under pressure, and through the bone graft apertures 321 in the superior and inferior components 320, 340.

As described above, the superior and inferior components 320, 340 are placed in the intervertebral space and the core component 360, 380 is positioned relative to the superior and inferior components as shown in FIG. 8A before the core component is inserted between the superior and inferior components. On initial insertion, the core component is placed generally between the superior and inferior components. During further insertion the core component is moved towards the inferior component until each first inferior core formation 368 is received in its respective groove 354 to thereby present a barrier to separation of the core component from the inferior component in the direction of the superior component. Otherwise and upon the superior component being adjacent the core component, the first and second lateral sides 366 are snugly received between the first and second superior component profiles 330, 332 to guide their relative movement as the core component is progressively inserted whilst the superior component is free to move away from and towards the core component in the direction of separation of the inferior and superior components.

When the core component 360, 380 is approaching full insertion between the inferior and superior components 320, 340 the inferior core rear formation 374 is received under the inferior component rear formation 356 to thereby present a barrier to the edge of the core component lifting from the inferior component. At the same time, the superior core rear formation 370 starts to engage with the superior component rear formation 334 and the two protrusions 376 of the superior core front formation start to engage with the two recesses 338 of the superior component front formation. Considering the superior core rear formation 370 further, the inclined surface 372 of the superior core rear formation 370 slides over the inclined surface 336 of the superior component rear formation 334 to draw the core component and the superior component together at their respective edges. Considering the two protrusions 376 of the superior core rear formation further, the inclined surfaces 378 of the protrusions 376 slide over the respective inclined surfaces 339 of the two recesses 338 of the superior component front formation to draw the core component and the superior component together at their respective edges.

When the core component 360, 380 is at full insertion, the protrusion 379 on the living hinge at the lower side 364 of the core component is urged by the inherent spring bias of the living hinge into the elongate aperture 358 in the inferior component. Reception of the protrusion 379 in the elongate aperture 358 presents a barrier to ejection of the core component from between the inferior and superior components.

Figure 10A:
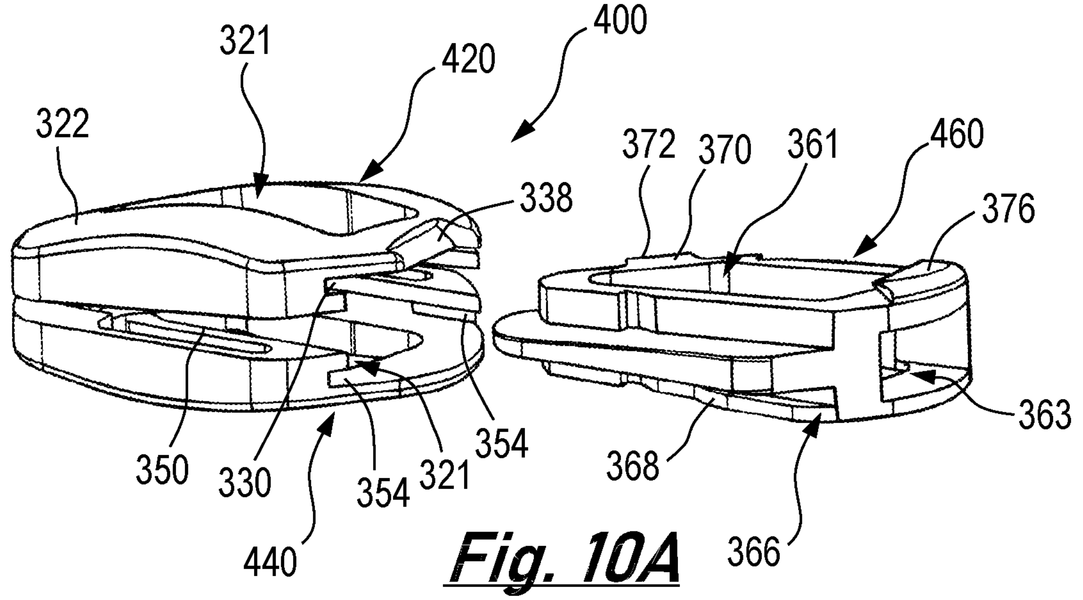
FIG. 10A shows the core component before insertion between the superior and inferior components according to the fifth embodiment.
Figure 10B:
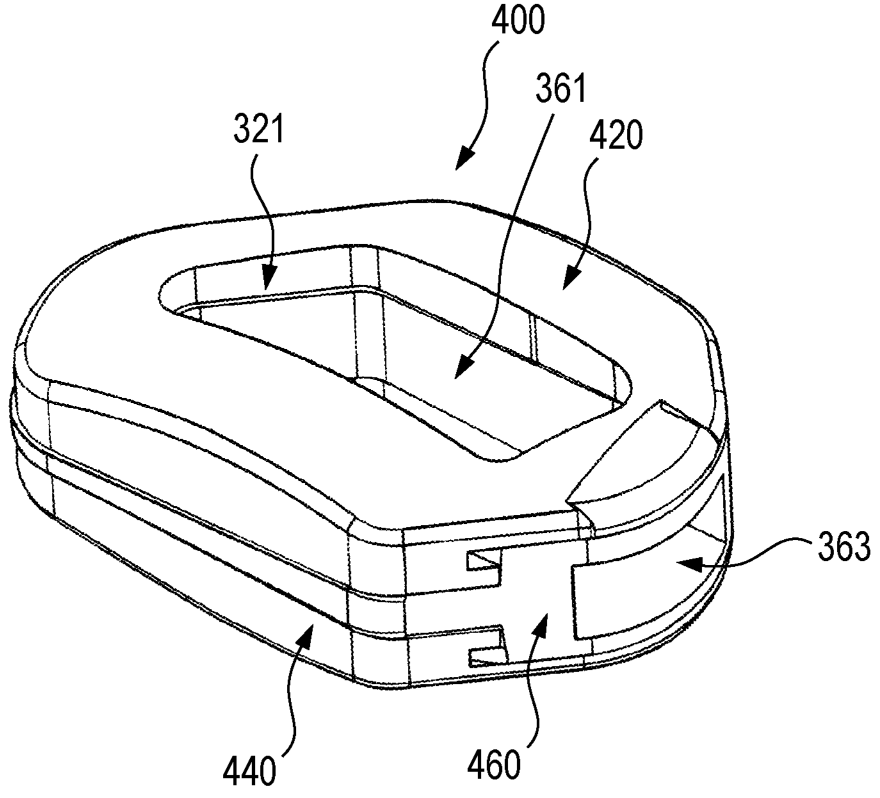
FIG. 10B shows the core component after insertion between the superior and inferior components according to the fifth embodiment.

A fifth embodiment of intervertebral fusion device 400 is shown in FIGS. 9A to 10B. The intervertebral fusion device 400 according to the fifth embodiment is an oblique lateral interbody fusion device. A superior component 420, an inferior component 440, and a core component 460 of the fifth embodiment are shown respectively in FIGS. 9A, 9B and 9C. The superior component 420 constitutes a superior endplate of the intervertebral fusion device 400 and the inferior component 440 constitutes an inferior endplate of the intervertebral fusion device 400. FIG. 10A shows the core component 460 of the fifth embodiment before insertion between the superior and inferior components 420, 440 of FIGS. 9A and 9B. FIG. 10B shows the core component 460 of the fifth embodiment after insertion between the superior and inferior components 420, 440 of FIGS. 9A and 9B. The superior component 420, the inferior component 440, and the core component 460 of the fifth embodiment are of different shape and dimensions to the third and fourth embodiments when viewed in plan whereby the fifth embodiment is configured for insertion into an intervertebral space from an oblique lateral direction. Otherwise, and except as described below, the fifth embodiment is configured in respect of key features in the same fashion as the third and fourth embodiments. Such key features are therefore indicated in FIGS. 9A to 10B by the same reference numerals as for the third and fourth embodiments and the reader's attention is directed to the preceding description for a description of such key features. In respect of differences, as can be seen from FIG. 9C, the core component 460 has one anterior formation 376 on its upper side instead of the two anterior formations 376 of the third and fourth embodiments. Correspondingly, the superior component 420 of the fifth embodiment has one recess 338 at its anterior edge instead of the two recesses of the third and fourth embodiments. Furthermore, the fifth embodiment lacks the third and fourth embodiments' combination of the protrusion 379 on the living hinge in the core component and the elongate aperture 358 in the inferior component.

Figure 11:
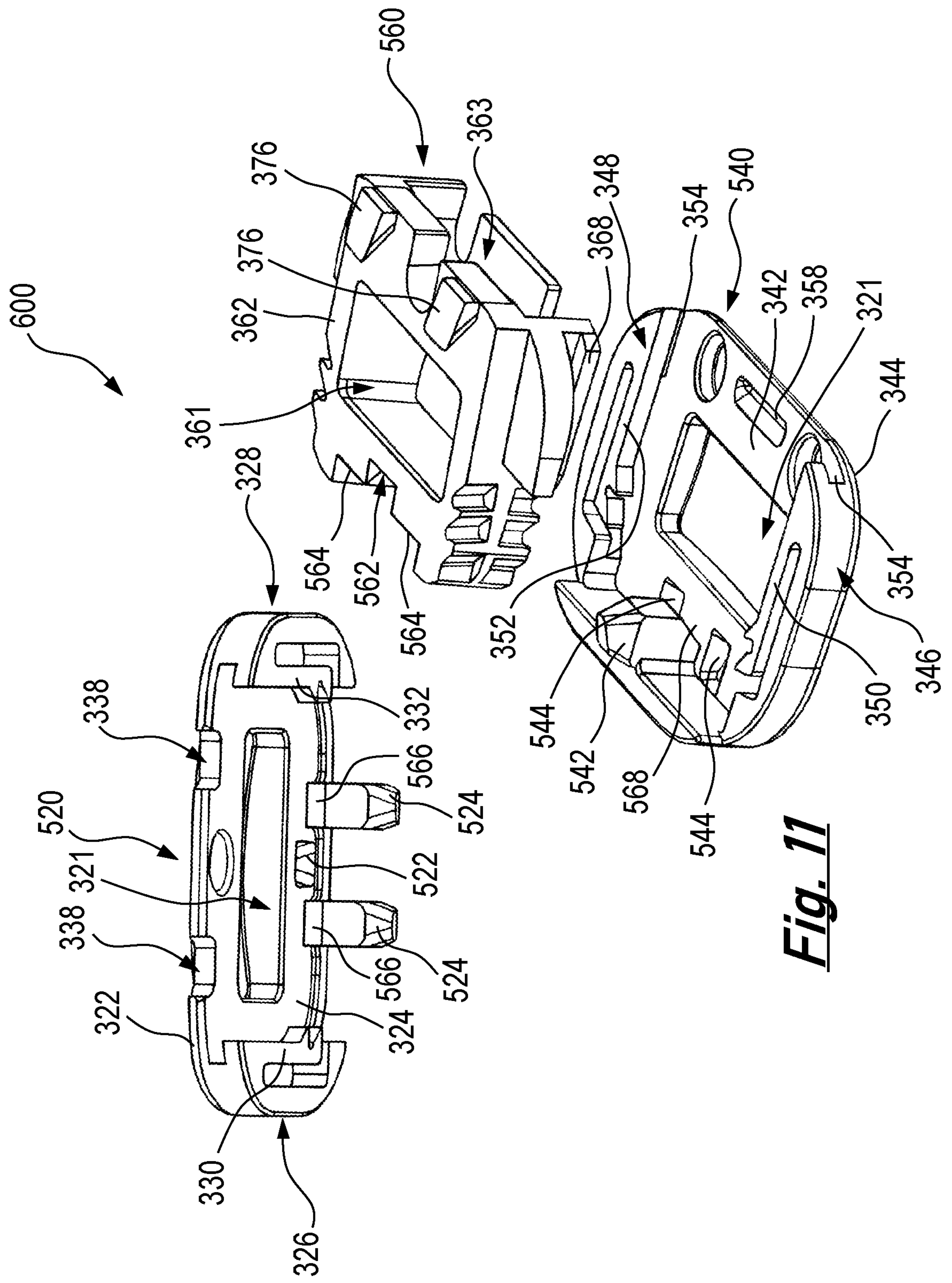
FIG. 11 shows an intervertebral fusion device according to a sixth embodiment.

A sixth embodiment of intervertebral fusion device 600 is shown in FIG. 11. The sixth embodiment 600 has a superior component 520, an inferior component 540, and a core component 560. The superior component 520 constitutes a superior endplate of the intervertebral fusion device 600 and the inferior component 540 constitutes an inferior endplate of the intervertebral fusion device 600. The sixth embodiment 600 is an anterior lumbar interbody fusion (ALIF) device like the third and fourth embodiments. Except as described below, the sixth embodiment is configured in respect of key features in the same fashion as the third and fourth embodiments. Such key features are therefore indicated in FIG. 11 by the same reference numerals as for the third and fourth embodiments and the reader's attention is directed to the preceding description for a description of such key features.

In respect of differences, as can be seen from FIG. 11, the sixth embodiment 600 lacks the combination of the superior core rear formation 370 and the superior component rear formation 334 and also the combination of the inferior core rear formation 374 and the inferior component rear formation 356. Instead, the inferior component 540 of the sixth embodiment 600 has an upwardly extending post 542 near its posterior edge and an aperture 544 on each side of the upwardly extending post 542. The superior component 520 of the sixth embodiment 600 has an aperture 522 near its posterior edge and a downwardly extending post 524 on each side of the aperture 522. The core component 560 of the sixth embodiment 600 has a core recess 562 which is centrally located in a posterior wall of the core component at the upper side 362. The sixth embodiment 600 is brought into use by positioning the inferior and superior components 520, 540 in the intervertebral space and such that each of the downwardly extending posts 524 is received in a respective one of the two apertures 544 in the inferior component and such that the upwardly extending post 542 is received in the aperture 522 of the superior component 520. Relative movement of the inferior and superior components 520, 540 is thus restricted whilst rotation of an end of each of the downwardly and upwardly extending posts 524, 542 in its respective aperture 522, 544 allows for the inferior and superior components to rotate towards the posterior aspect in relation to each other. The core component 560 is then inserted between the inferior and superior components 520, 540. When the core component 560 is fully received between the inferior and superior components 520, 540, the side of the upwardly extending post 542 is received in the core recess 562. Furthermore, when the core component is fully received, a leading sharp edge 564 on each side of the core recess 562 and at the upper side 362 is received in a recess 566 defined towards the proximal end of a respective one of the two downwardly extending posts 524, to thereby present resistance to separation of the superior component 520 and the core component 560 from each other at the posterior aspect. The upwardly extending post 542 on the inferior component 540 defines a recess 568 towards its proximal end. A sharp edge (not seen in FIG. 11) at the lower side and the posterior aspect of the core component 560 is received in the recess 568 in the upwardly extending post 542 to thereby present resistance to separation of the inferior component 540 and the core component 560 from each other at the posterior aspect.

Figure 12A:
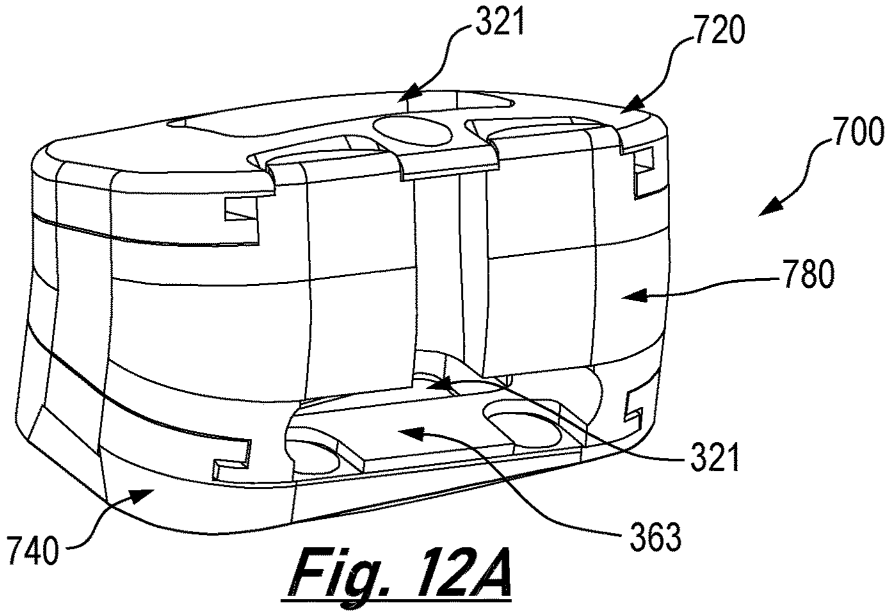
FIG. 12A is a perspective view of a seventh embodiment of the present invention.
Figure 12B:
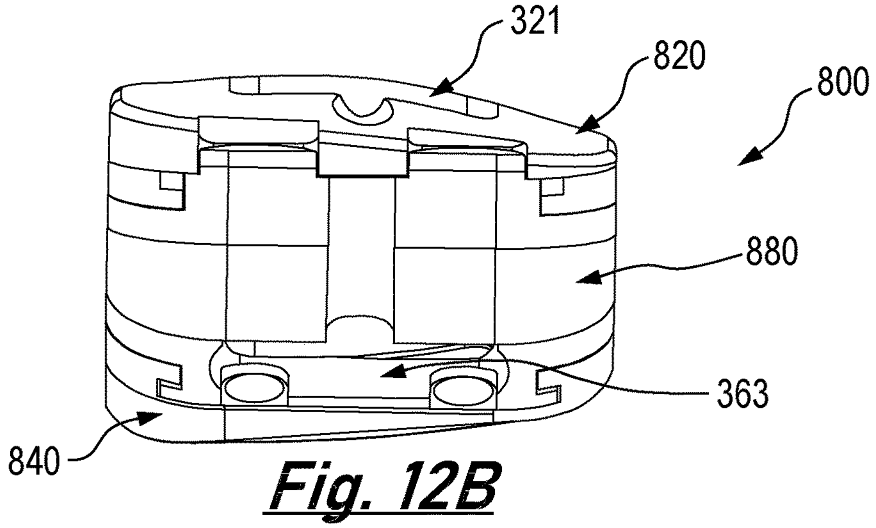
FIG. 12B is a perspective view of an eighth embodiment of the present invention.
Figure 12C:
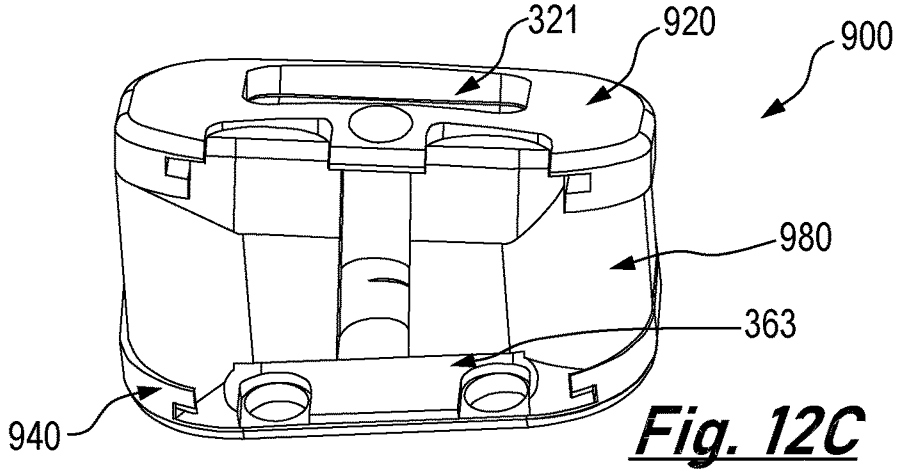
FIG. 12C is a perspective view of a ninth embodiment of the present invention.

Seventh, eighth and ninth embodiments of anterior lumbar interbody fusion (ALIF) devices 700, 800, 900 are shown in FIGS. 12A, 12B, and 12C respectively. Some key features of the seventh, eighth and ninth embodiments in common with the third embodiment are indicated in FIGS. 12A, 12B, and 12C by the same reference numerals as for the third embodiment and the reader's attention is directed to the preceding description for a description of such key features. The fourth embodiment of anterior lumbar interbody fusion (ALIF) device 310 shown in FIGS. 8A and 8B decreases in height from left to right in the coronal direction, i.e. in the direction orthogonal to the direction of insertion of the core component 380 between the superior and inferior components 320, 340, which is in the sagittal direction, and to the direction of separation of the superior and inferior components from each other. The decrease in height of the fourth embodiment of anterior lumbar interbody fusion (ALIF) device 310 is achieved by the superior component 320 decreasing in height from left to right in the coronal direction. With reference to FIG. 7A, the decrease in height of the superior component 320 is achieved by inclination of the superior component top side 322 and the superior component bottom side 324 to each other. In another example, the decrease in height of the anterior lumbar interbody fusion (ALIF) device is from right to left, which is achieved by decrease in height of the core component from right to left.

The seventh embodiment of anterior lumbar interbody fusion (ALIF) device 700 shown in FIG. 12A comprises a superior component 720, an inferior component 740, and a core component 780. The seventh embodiment of anterior lumbar interbody fusion (ALIF) device 700 is a further example in which there is decrease in height from left to right in the coronal direction. The decrease in height is achieved by the inferior component 740 decreasing in height from left to right in the coronal direction. With reference to FIG. 7B, the decrease in height of the inferior component 740 is achieved by inclination of the inferior component top side 342 and the inferior component bottom side 344 to each other. The effect of the seventh embodiment is the same as the effect of the fourth embodiment.

The eighth embodiment of anterior lumbar interbody fusion (ALIF) device 800 shown in FIG. 12B comprises a superior component 820, an inferior component 840, and a core component 880. The eighth embodiment of anterior lumbar interbody fusion (ALIF) device 800 is a further example in which there is decrease in height from left to right in the coronal direction. The decrease in height is achieved by each of the superior component 820 and the inferior component 840 decreasing in height from left to right in the coronal direction. With reference to FIG. 7A, the decrease in height of the superior component 820 is achieved by inclination of the superior component top side 322 and the superior component bottom side 324 to each other. With reference to FIG. 7B, the decrease in height of the inferior component 840 is achieved by inclination of the inferior component top side 342 and the inferior component bottom side 344 to each other. The effect of the eighth embodiment is the same as the effect of the fourth and seventh embodiments.

The ninth embodiment of anterior lumbar interbody fusion (ALIF) device 900 shown in FIG. 12C comprises a superior component 920, an inferior component 940, and a core component 980. The ninth embodiment of anterior lumbar interbody fusion (ALIF) device 900 is a further example in which there is decrease in height from left to right in the coronal direction. The decrease in height is achieved by the core component 980 decreasing in height from left to right in the coronal direction. With reference to FIG. 7C, the decrease in height of the core component 980 is achieved by inclination of the upper side 362 and the lower side 364 to each other. The effect of the ninth embodiment is the same as the effect of the fourth, seventh and eighth embodiments. In further embodiments, the core component decreases in height in the coronal direction and at least one of the superior and inferior components decreases in height in the coronal direction. As described above with reference to FIGS. 7 to 8B, the core component 360, 380 has the shape of a frustrum of a wedge whereby the anterior lumbar interbody fusion (ALIF) device decreases in height in the sagittal direction. Embodiments of the anterior lumbar interbody fusion (ALIF) device may thus decrease in height in each of the coronal and sagittal directions.

Figure 13A:
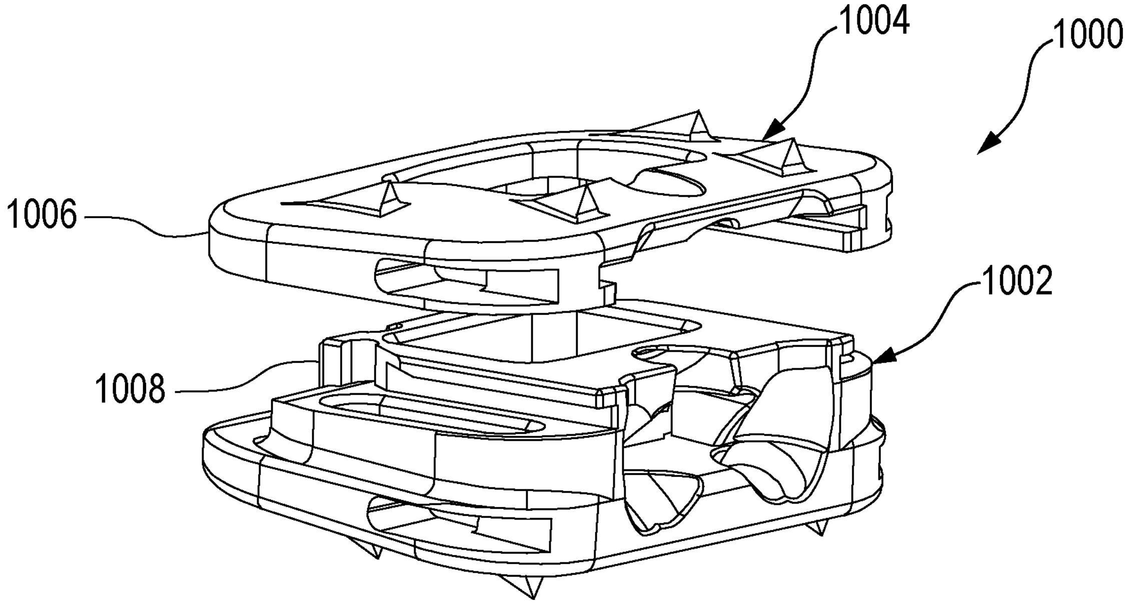
FIG. 13A is an exploded perspective view of a tenth embodiment of the present invention.
Figure 13B:
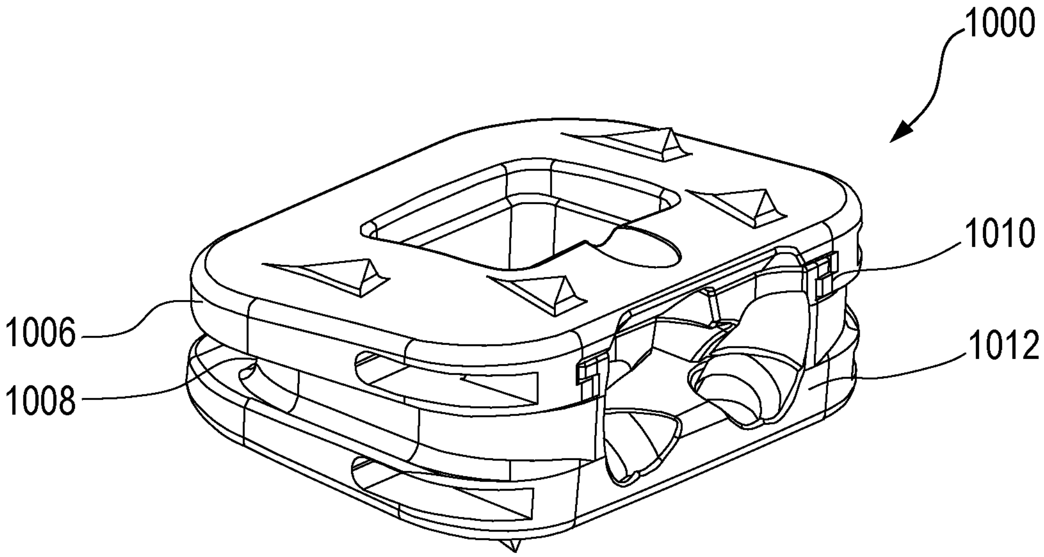
FIG. 13B is a perspective view of the tenth embodiment when assembled.

A tenth embodiment 1000 of the present invention is shown in FIGS. 13A and 13B. FIG. 13A is an exploded perspective view of the tenth embodiment 1000 and FIG. 13B is a perspective view of the tenth embodiment when assembled. Unlike previous embodiments which comprise a core component and inferior and superior components (which constitute inferior and superior endplates), the present embodiment comprises a core component 1002 and only one endplate 1004 which functions in the present application as a superior endplate. The core component 1002 is in effect an inferior endplate/component according to the previous embodiments which is integrally formed with a core component according to the previous embodiments. The core component 1002 and the endplate 1004 are structured for their inter-engagement as described with reference to the previous embodiments.

Key features of the tenth embodiment 1000 will now be described. The endplate 1004 is of a length in the anterior-posterior direction such that its posterior end 1006 extends beyond the posterior end 1008 of the central part of the core component 1002. This is in contrast to earlier embodiments, such as those of FIGS. 12A to 12C, in which the endplates are shorter such that the endplates do not extend beyond their respective core component. The present core component 1002 and the endplate 1004 are structured in respect of inter-engaging features described for the earlier embodiments such that a surface 1010 at the anterior end of the endplate 1004 is aligned with a surface 1012 at the anterior end of the core component 1002 when the core component and endplate are locked together to thereby define a datum at the anterior end from which measurements can be made by the clinician. The earlier embodiments likewise define a datum at their anterior ends, as can be seen from FIGS. 4B, 6B, 8B, 10B, 12A, 12B and 12C.

Figure 14A:
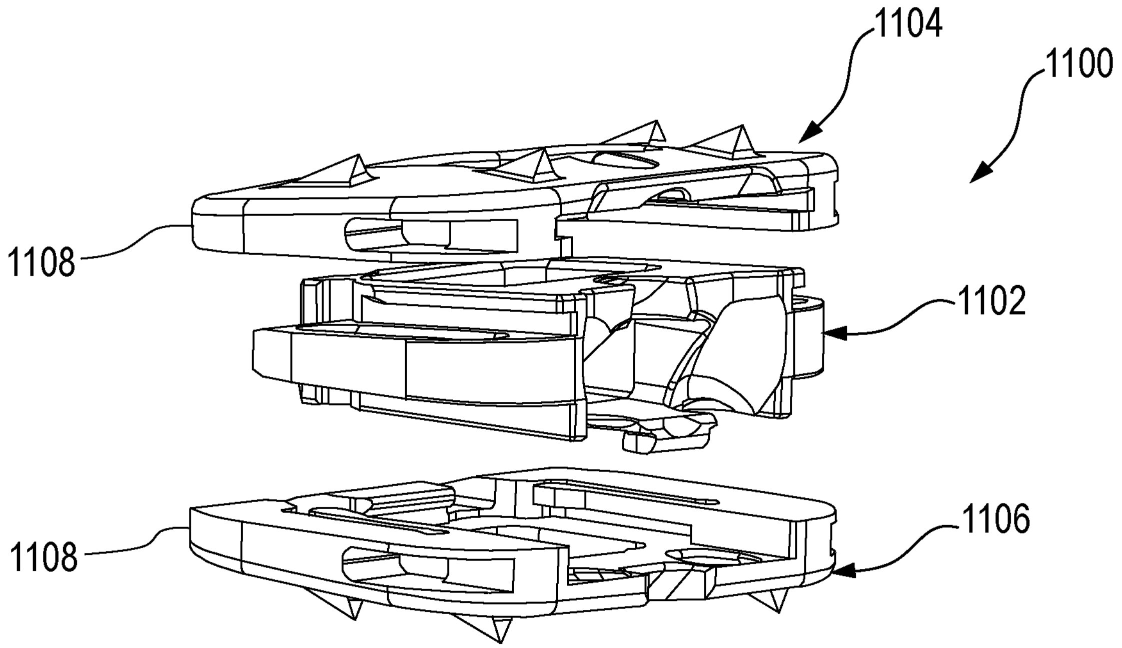
FIG. 14A is an exploded perspective view of an eleventh embodiment of the present invention.
Figure 14B:
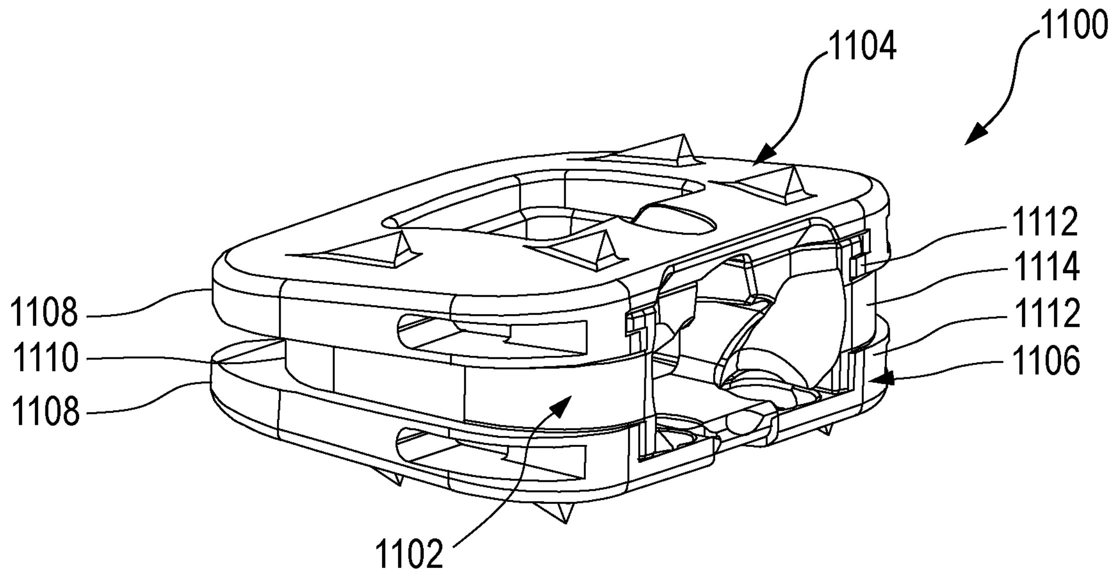
FIG. 14B is a perspective view of the eleventh embodiment when assembled.

An eleventh embodiment 1100 of the present invention is shown in FIGS. 14A and 14B. FIG. 14A is an exploded perspective view of the eleventh embodiment 1100 and FIG. 14B is a perspective view of the eleventh embodiment when assembled.

When assembled as per FIG. 14B, the eleventh embodiment appears the same as the tenth embodiment when assembled as per FIG. 13B. However, as can be seen from the exploded view of FIG. 14A, the eleventh embodiment comprises a core component 1102, a superior endplate 1104 and an inferior endplate 1106 whereby the eleventh embodiment is a three component intervertebral fusion device whereas the tenth embodiment is a two component intervertebral fusion device. The core component 1102 and the superior and inferior endplates 1104, 1106 are structured for their inter-engagement as described with reference to the previous embodiments.

Key features of the eleventh embodiment 1100 will now be described. Each of the superior and inferior endplates 1104, 1106 is of a length in the anterior-posterior direction such that its posterior end 1108 extends beyond the posterior end 1110 of the core component 1102 when the intervertebral fusion device is assembled. As per the tenth embodiment 1000, this is in contrast to earlier embodiments, such as those of FIGS. 12A to 12C, in which the endplates are shorter such that the endplates do not extend beyond their respective core component when the intervertebral fusion device is assembled. The present core component 1102 and the superior and inferior endplates 1104, 1106 are structured in respect of inter-engaging features described for the earlier embodiments such that a surface 1112 at the anterior end of each of the superior and inferior endplates is aligned with a surface 1114 at the anterior end of the core component 1102 when the core component and the endplates are locked together to thereby define a datum at the anterior end from which measurements can be made by the clinician.

Figure 15A:
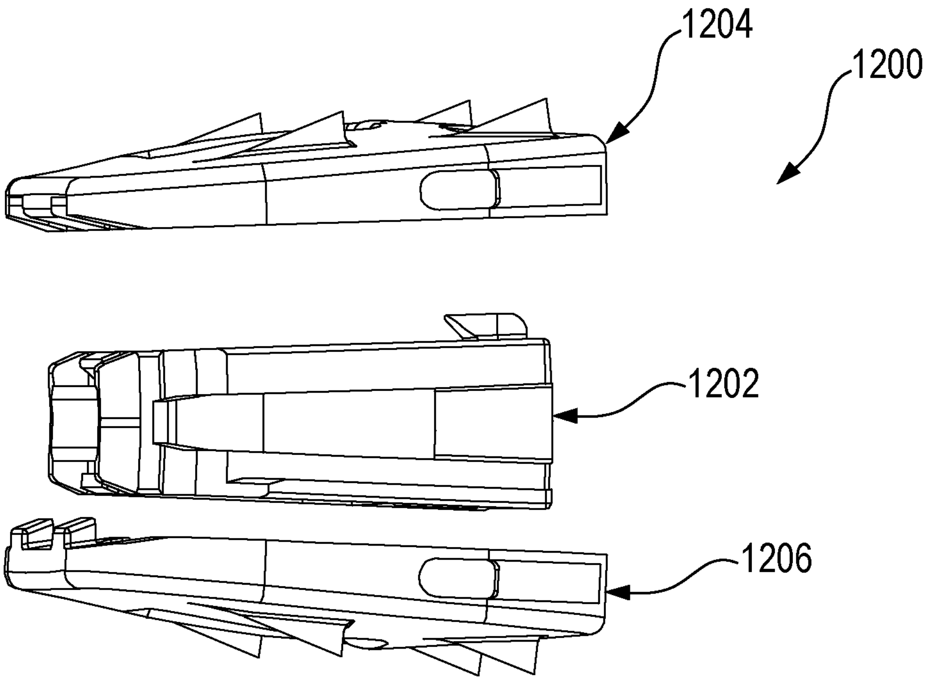
FIG. 15A is an exploded perspective view of a twelfth embodiment of the present invention.
Figure 15B:
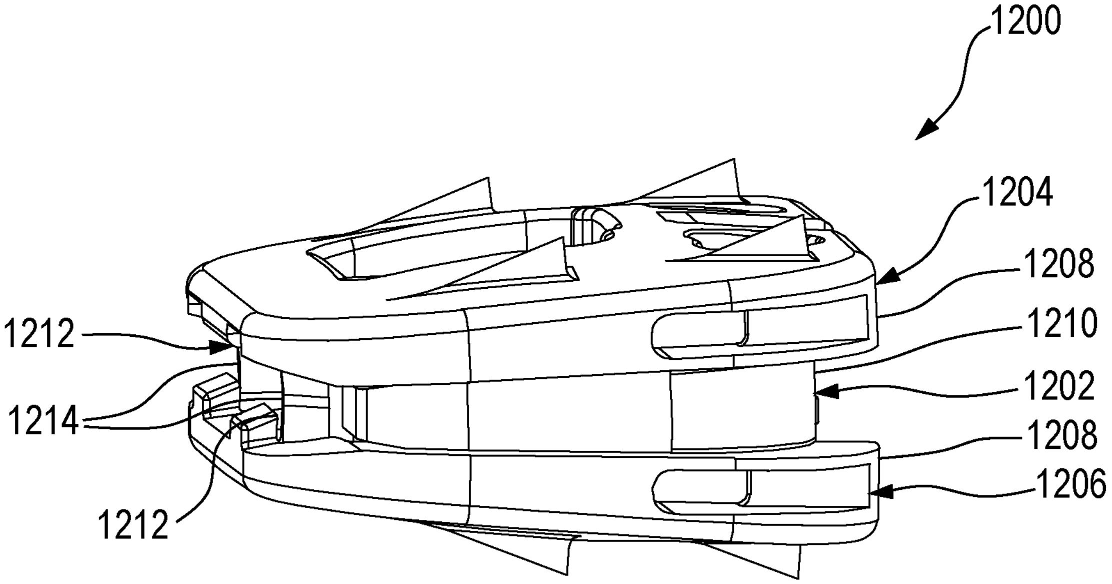
FIG. 15B is a perspective view of the twelfth embodiment when assembled.

A twelfth embodiment 1200 of the present invention is shown in FIGS. 15A and 15B. FIG. 15A is an exploded perspective view of the twelfth embodiment 1200 and FIG. 15B is a perspective view of the twelfth embodiment when assembled. Like the eleventh embodiment 1100, the twelfth embodiment 1200 is a three component intervertebral fusion device. The twelfth embodiment 1200 comprises a core component 1202, a superior endplate 1204 and an inferior endplate 1206. The core component 1202 and the superior and inferior endplates 1204, 1206 are structured for their inter-engagement as described with reference to the previous embodiments.

Key features of the twelfth embodiment 1200 will now be described. Each of the superior and inferior endplates 1204, 1206 is of a length in the anterior-posterior direction such that its anterior end 1208 extends beyond the anterior end 1210 of the core component 1202. The core component 1202 and the superior and inferior endplates 1204, 1206 are structured in respect of inter-engaging features described for the earlier embodiments such that a surface 1212 towards the posterior end of each of the superior and inferior endplates is adjacent a surface 1214 towards the posterior end of the core component 1202 when the core component and the endplates are locked together to thereby define a datum towards the posterior end from which measurements can be made by the clinician.

Figure 16A:
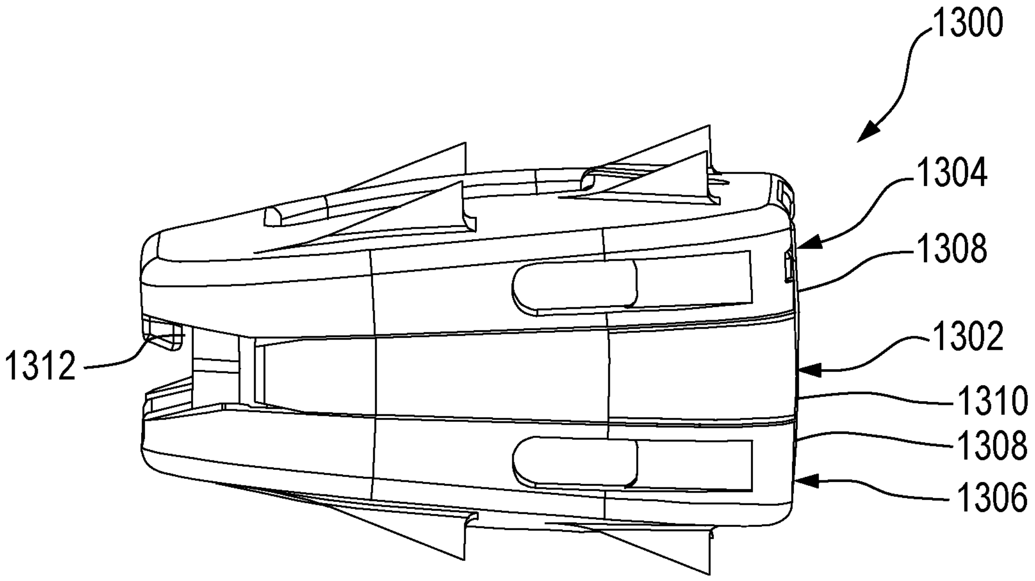
FIG. 16A is a perspective view of a thirteenth embodiment of the present invention when assembled.
Figure 16B:
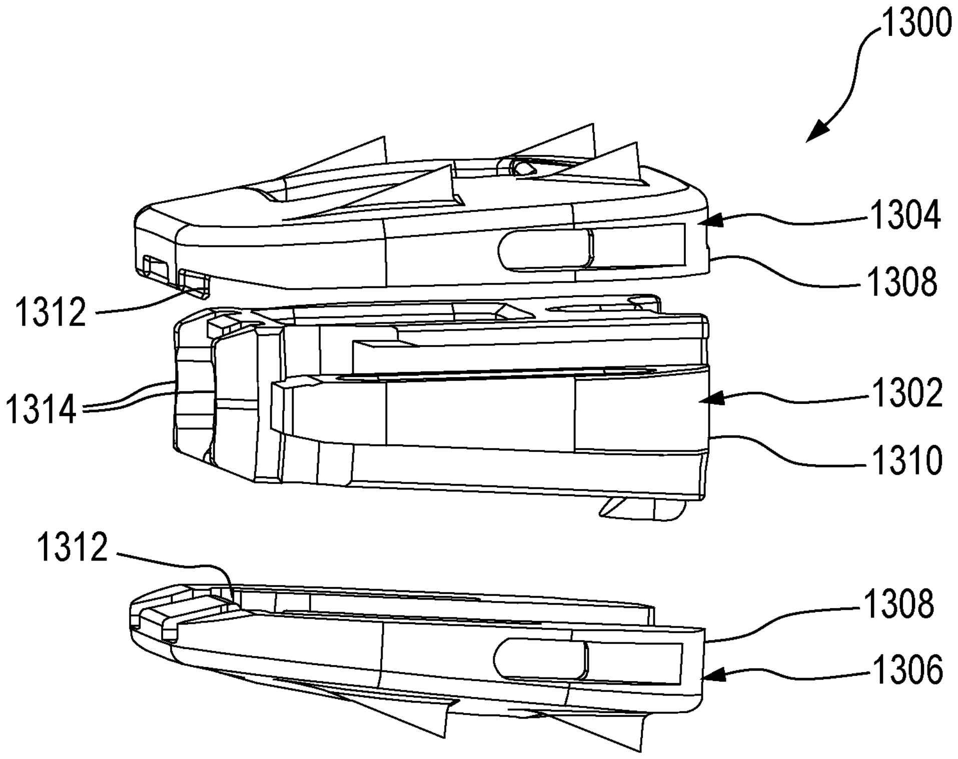
FIG. 16B is an exploded perspective view of the thirteenth embodiment.

A thirteenth embodiment 1300 of the present invention is shown in FIGS. 16A and 16B. FIG. 16A is a perspective view of the thirteenth embodiment 1200 when assembled and FIG. 16B is an exploded perspective view of the thirteenth embodiment. Like the twelfth embodiment 1200, the thirteenth embodiment 1300 comprises a core component 1302, a superior endplate 1304 and an inferior endplate 1306 whereby the thirteenth embodiment is a three component intervertebral fusion device. The core component 1302 and the superior and inferior endplates 1304, 1306 are structured for their inter-engagement as described with reference to the previous embodiments.

Key features of the thirteenth embodiment 1300 will now be described. Each of the superior and inferior endplates 1304, 1306 is of a length in the anterior-posterior direction such that its anterior end 1308 is aligned with the anterior end 1310 of the core component 1102 when the intervertebral fusion device is assembled. This is in contrast to the twelfth embodiment 1200 in which the endplates are longer such that they extend beyond the core component at its anterior end. The present core component 1302 and the superior and inferior endplates 1304, 1306 are structured in respect of inter-engaging features described for the earlier embodiments such that a surface 1312 towards the posterior end of each of the superior and inferior endplates is adjacent a surface 1314 towards the posterior end of the core component 1302 when the core component and the endplates are locked together to thereby define a datum towards the posterior end from which measurements can be made by the clinician.

A fourteenth embodiment of the present invention is constituted by a kit of parts from which selection is made to form an intervertebral fusion device. The kit of parts comprises a plurality of different endplates, and in some forms a plurality of different superior endplates and a plurality of different inferior endplates, and a core component. In further forms, the kit further comprises a plurality of different core components. The intervertebral fusion device is formed by selecting one of the plurality of different endplates depending on clinical requirements. Where there are a plurality of different superior endplates and a plurality of different inferior endplates, one of the different superior endplates is selected and one of the different inferior endplates is selected. Where there are plural different core components, one of the core components is selected depending on clinical requirements.

The plurality of endplates differ from one another in respect of at least one of material composition, such as a coating thereon, configuration, such as in respect of coronal slope, and dimensions, such as length in the anterior-posterior direction and/or width in the transverse direction. According to one example, the plurality of endplates comprises the endplates of FIGS. 12A, 12B and 14A. According to another example, the plurality of endplates comprises the endplates of FIGS. 15A and 16B. The plurality of core components differ from one another in respect of at least one of material composition, configuration, such as in respect of lordotic angle, and dimensions, such as height. For example, the plurality of core components comprises the core components of FIGS. 12A, 12C and 14A.

Each of the plurality of endplates in the kit of parts defines a bone graft aperture, as described above, which is open at top and bottom surfaces of the endplate and extends between the top and bottom surfaces. The bone graft apertures are of substantially the same dimensions as one another when the plurality of endplates are in plan view. The or each core component defines a bone graft material holding space having a holding space opening in one of a core component top surface and a core component bottom surface of the core component. When the core component is in plan view, the holding space opening is of substantially the same dimensions as each of the bone graft apertures. Furthermore, the core component(s) and endplates are structured in respect of respective features that provide for inter-engagement and locking together of core component and endplates such that the holding space opening is substantially coextensive with the bone graft aperture of the selected endplate in plan view and when the core component is engaged with and in registration with the selected endplates regardless of which of the plurality of endplates is selected.

The invention claimed is:

1. A kit of parts from which selection is made to form an intervertebral fusion device, the kit of parts comprising:

a plurality of different endplates each of which is configured to be received in an intervertebral space defined between first and second vertebrae, the plurality of different endplates consisting of one of different superior endplates and different inferior endplates; and a core component configured to engage with a different one of the plurality of different endplates at respective different times, the core component engaging with a selected one of the plurality of different endplates when the selected endplate and the core component are received in the intervertebral space, wherein each of the plurality of different endplates defines a bone graft aperture which is open at top and bottom surfaces of the endplate and extends between the top and bottom surfaces, the bone graft apertures being of substantially the same dimensions as one another when the plurality of different endplates are in plan view, the core component defines a bone graft material holding space having a holding space opening in one of a core component top surface and a core component bottom surface of the core component, when the core component is in plan view the holding space opening is of substantially the same dimensions as each of the bone graft apertures, and the holding space opening is substantially coextensive with the bone graft aperture of the selected endplate in plan view and when the core component is engaged with and in registration with the selected endplate.

2. The kit of parts according to claim 1, wherein the plurality of different endplates differ from one another in at least one of material composition, configuration and dimensions.

3. The kit of parts according to claim 1, wherein the plurality of different endplates consists of different superior endplates and the holding space opening is in the core component top surface, the core component top surface configured to face the bottom surface of the selected endplate when one of the superior endplates is selected to be in engagement with the core component.

4. The kit of parts according to claim 3, further comprising a further plurality of different endplates consisting of different inferior endplates and a further holding space opening in the core component bottom surface, the core component bottom surface configured to face the top surface of the selected endplate when one of the inferior endplates is selected to be in engagement with the core component.

5. The kit of parts according to claim 1, comprising a plurality of different core components, each of the plurality of different core components defining a bone graft material holding space having a holding space opening in one of a core component top surface and a core component bottom surface of the core component, each holding space opening having substantially the same dimensions as one another when the plurality of different core components are in plan view.

6. The kit of parts according to claim 5, wherein the intervertebral fusion device comprises a selected one of the plurality of different core components, the plurality of different core components differing from one another in at least one of material composition, configuration, and dimensions.

7. The kit of parts according to claim 1, wherein the core component is configured for inter-engagement with each endplate.

8. The kit of parts according to claim 7, wherein the core component is configured and each of the plurality of different endplates is configured to prevent movement apart of the core component and the selected endplate in a direction orthogonal to a direction of insertion of the intervertebral fusion device into the intervertebral space and orthogonal to a transverse direction.

9. The kit of parts according to claim 8, wherein the core component is configured and each of the plurality of different endplates is configured to prevent movement of the core component and the selected endplate relative to each other in the transverse direction.

10. The kit of parts according to claim 9, wherein the core component and the selected endplate are configured for relative sliding movement in the direction of insertion of the intervertebral fusion device into the intervertebral space.

11. The kit of parts according to claim 7, wherein core component features of the core component that provide for inter-engagement with any one of the plurality of different endplates provide for inter-engagement with each of the other endplates of the plurality of different endplates, and each of the plurality of different endplates comprises endplate features for inter-engagement with the core component with the endplate features corresponding structurally from endplate to endplate of the plurality of different endplates.

12. The kit of parts according to claim 1, wherein the core component and each endplate are configured to lock together when they are in registration with each other, the core component and each endplate configured to lock together to prevent movement in at least one of a direction opposite the direction of insertion of the intervertebral fusion device into the intervertebral space, the transverse direction and the direction of separation of the first and second vertebrae.

13. The kit of parts according to claim 12, wherein the core component and each endplate are configured for relative sliding movement, the core component and each endplate configured to lock together to prevent movement in the direction opposite the direction of insertion of the intervertebral fusion device into the intervertebral space.

14. The kit of parts according to claim 12, wherein core component features of the core component that provide for locking with any one of the plurality of different endplates provide for locking with each of the other endplates of the plurality of different endplates, and each of the endplates comprises endplate features for locking with the core component with the endplate features corresponding structurally from endplate to endplate of the plurality of different endplates.

15. The kit of parts according to claim 1, wherein the bone graft material holding space is defined by walls on at least three of four sides, a fourth side of the bone graft material holding space is open at least in part to define a bone graft port wherethrough bone graft material is injectable into the bone graft material holding space, and a wall of the fourth side and which defines the bone graft port lies in a plane which is substantially orthogonal to a direction of insertion of the core component into the intervertebral space.

16. The kit of parts according to claim 1, wherein the core component and each of the plurality of different endplates is configured such that a first surface on an outer surface of the core component towards a posterior aspect of the core component is adjacent or aligned with a second surface on an outer surface of each of the endplates towards their posterior aspects and when the core component is in registration with the selected endplate to thereby provide a datum towards the posterior aspect from which measurement can be made, and whereby there is adjacency or alignment of first and second surfaces regardless of which of the plurality of different endplates has been selected.

17. The kit of parts according to claim 16, wherein the plurality of different endplates differ from each other in at least one of shape and dimensions, and the plurality of different endplates are configured such that each of their second surfaces is adjacent or aligns with the first surface when the core component and each endplate are in registration.

18. The kit of parts according to claim 1, wherein the holding space opening is substantially coextensive with the bone graft aperture at each lateral side of the holding space opening.

19. The kit of parts according to claim 1, wherein the holding space opening is substantially coextensive with the bone graft aperture around substantially all of the holding space opening.

20. A kit of parts from which selection is made to form an intervertebral fusion device, the kit of parts comprising:

a plurality of different endplates each of which is configured to be received in an intervertebral space defined between first and second vertebrae, the plurality of different endplates consisting of one of different superior endplates and different inferior endplates; and a core component configured to inter-engage with a different one of the plurality of different endplates at respective different times, the core component inter-engaging with a selected one of the plurality of different endplates when the selected endplate and the core component are received in the intervertebral space, wherein each of the plurality of different endplates defines a bone graft aperture, the core component defines a bone graft material holding space having a holding space opening in one of a core component top surface and a core component bottom surface of the core component, the core component comprises core component features which inter-engage with endplate features of each of the plurality of different endplates whereby the core component inter-engages with the selected endplate, the endplate features corresponding structurally from endplate to endplate of the plurality of different endplates, the holding space opening is substantially coextensive with the bone graft aperture of the selected endplate in plan view regardless of which of the plurality of different endplates is selected and when the core component is moved to its furthest extent in the anterior to posterior direction relative to the selected endplate when the core component is inter-engaged with the selected endplate.

21. The kit of parts according to claim 20, wherein the holding space opening is substantially coextensive with the bone graft aperture at each lateral side of the holding space opening.

22. The kit of parts according to claim 20, wherein the holding space opening is substantially coextensive with the bone graft aperture around substantially all of the holding space opening.

23. A method of installing an intervertebral fusion device in an intervertebral space between first and second adjacent vertebrae, the method comprising:

selecting one of a plurality of different endplates comprised in a kit of parts, the plurality of different endplates consisting of one of different superior endplates and different inferior endplates, each of the plurality of different endplates configured to be received in an intervertebral space defined between first and second vertebrae, and each of the plurality of different endplates defining a bone graft aperture which is open at top and bottom surfaces of the endplate and extends between the top and bottom surfaces, the bone graft apertures being of substantially the same dimensions as one another when the plurality of different endplates are in plan view;

engaging a core component comprised in the kit of parts with the selected endplate to form an intervertebral fusion device, the core component configured to engage with a different one of the plurality of different endplates at respective different times, the core component defining a bone graft material holding space having a holding space opening in one of a core component top surface and a core component bottom surface of the core component; and installing the intervertebral fusion device in the intervertebral space such that the core component engages with the selected endplate when in the intervertebral space, wherein the holding space opening is of substantially the same dimensions as each of the bone graft apertures when the core component and the plurality of different endplates are in plan view, and the holding space opening is substantially coextensive with the bone graft aperture of the selected endplate in plan view and when the core component is engaged with and in registration with the selected endplate.

* * * * *